US010925853B2

(12) United States Patent
Bruun et al.

(10) Patent No.: US 10,925,853 B2
(45) Date of Patent: Feb. 23, 2021

(54) ORAL CANNABINOID TABLET

(71) Applicant: NordicCan A/S, Vejle (DK)

(72) Inventors: Heidi Ziegler Bruun, Vejle O (DK); Dorthe Schackinger Boesen, Vejle (DK); Ane Eriksen, Vejle (DK); Helle Wittorff, Vejle Ost (DK)

(73) Assignee: NORDICCAN A/S, Vejle (DK)

( * ) Notice: Subject to any disclaimer, the term of this patent is extended or adjusted under 35 U.S.C. 154(b) by 0 days.

(21) Appl. No.: 16/386,477

(22) Filed: Apr. 17, 2019

(65) Prior Publication Data

US 2020/0330423 A1    Oct. 22, 2020

(51) Int. Cl.
| | | |
|---|---|---|
| *A61K 31/352* | (2006.01) | |
| *A61K 31/05* | (2006.01) | |
| *A61K 31/192* | (2006.01) | |
| *A61K 9/00* | (2006.01) | |
| *A61K 9/20* | (2006.01) | |

(52) U.S. Cl.
CPC .......... *A61K 31/352* (2013.01); *A61K 9/0056* (2013.01); *A61K 9/2018* (2013.01); *A61K 31/05* (2013.01); *A61K 31/192* (2013.01)

(58) Field of Classification Search
CPC .... A61K 31/352; A61K 31/195; A61K 31/05; A61K 9/0056; A61K 9/2018
See application file for complete search history.

(56) References Cited

U.S. PATENT DOCUMENTS

| | | | |
|---|---|---|---|
| 5,536,526 A * | 7/1996 | Virtanen | A23G 3/346 426/658 |
| 6,730,330 B2 | 5/2004 | Whittle et al. | |
| 8,735,374 B2 | 5/2014 | Zerbe et al. | |
| 2010/0034888 A1 | 2/2010 | Pellikaan et al. | |
| 2014/0328973 A1* | 11/2014 | Nielsen | A23G 4/08 426/2 |
| 2016/0220593 A1 | 8/2016 | Anastassov et al. | |
| 2017/0157041 A1 | 6/2017 | Goldner | |
| 2017/0312261 A1* | 11/2017 | Changoer | A61K 31/05 |
| 2017/0368020 A1 | 12/2017 | Estey et al. | |
| 2018/0042842 A1 | 2/2018 | Whittle et al. | |
| 2018/0071350 A1 | 3/2018 | Kolsky | |
| 2018/0221304 A1 | 8/2018 | Small-Howard et al. | |

FOREIGN PATENT DOCUMENTS

| | | |
|---|---|---|
| CA | 2664311 C | 3/2008 |
| CA | 2664315 A1 | 3/2008 |
| EP | 2061427 B1 | 7/2011 |
| EP | 2314284 B1 | 2/2017 |
| WO | WO2016/126592 A1 | 8/2016 |
| WO | WO2017/183011 A1 | 10/2017 |
| WO | WO2017/223309 A1 | 12/2017 |
| WO | WO2018/022669 A1 | 2/2018 |
| WO | WO2018/089863 A1 | 5/2018 |
| WO | WO2018/142403 A1 | 8/2018 |
| WO | WO2018/144637 A1 | 8/2018 |

\* cited by examiner

*Primary Examiner* — Sarah Pihonak
(74) *Attorney, Agent, or Firm* — Gregory M. Howison

(57) ABSTRACT

The present invention relates to an oral tablet for delivery of cannabinoids to mucosal surfaces comprising a population of particles and one or more cannabinoids, the population of particles comprising a) directly compressible (DC) sugar alcohol particles and b) non-directly compressible (non-DC) sugar alcohol particles, the non-DC particles providing the tablet with a plurality of discrete non-DC areas.

27 Claims, 3 Drawing Sheets

Figure 4:
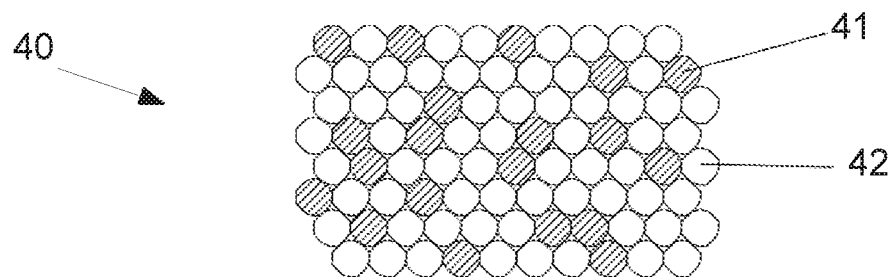

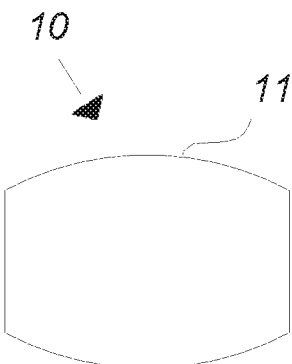
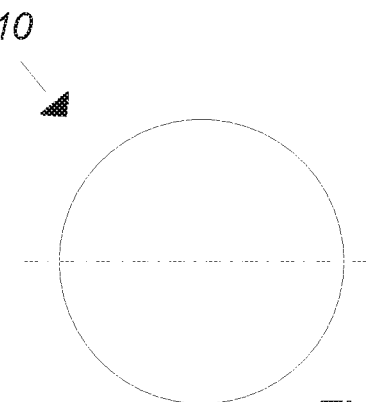
Fig.1a            Fig.1b
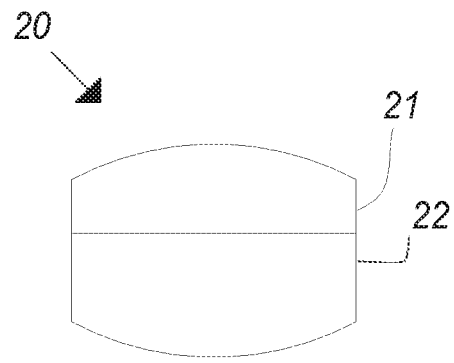
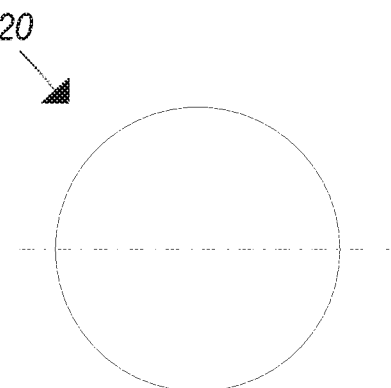
Fig.2a            Fig.2b
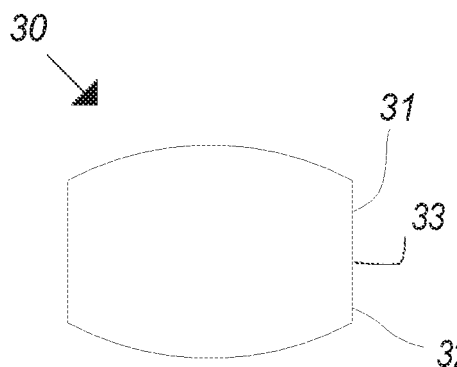
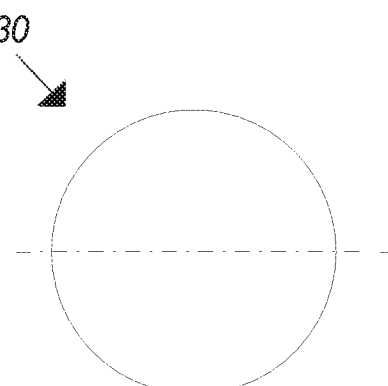
Fig.3a            Fig.3b

ORAL CANNABINOID TABLET

FIELD OF THE INVENTION

The invention relates to the field of cannabinoids. In particular, the invention relates to an oral cannabinoid tablet for alleviation or treatment of a condition. More specifically, the oral tablet is particularly suitable for delivery of one or more cannabinoids to mucosal surfaces.

BACKGROUND OF THE INVENTION

Oral administration of cannabinoids is a common route of administration. However, cannabinoids are highly lipophilic, meaning that they are soluble in lipids and some organic solvents while being substantially insoluble or only sparsely soluble in water. Cannabinoids are soluble in highly non-polar solvents. Some of these solvents are pharmaceutically unacceptable, and the pharmaceutically acceptable solvents need to be used in high concentrations to produce solutions.

In the field of cannabinoids, oral tablets have been disclosed as a vehicle for delivery of cannabinoids for alleviation or treatment of medical conditions, such as medical conditions associated with pain. While focus has generally been directed to clinical studies supporting various effects of cannabinoids to the human body, only limited attention is given in the prior art of cannabinoids on improving such tablet formulations for the purpose of improving release of cannabinoids.

Particularly, less attention is given on the benefits of chewable tablet formulations that may help in obtaining a release characteristic of cannabinoids that offers increased convenience and effectiveness. One of these release characteristics is increased generation of saliva upon chewing. Increased saliva generation and particularly an experience of increased saliva generation upon administration may have some pronounced benefits for delivery of cannabinoids to mucosal surfaces.

Cannabinoids are a group of chemicals found in *Cannabis sativa, Cannabis indica, Cannabis ruderalis*, Marijuana plant and related plant species. They are known to activate cannabinoid receptors (CB1 and CB2). These chemicals are also produced endogenously in humans and other animals. Cannabinoids are cyclic molecules exhibiting particular properties such as being lipophilic, have the ability to easily cross the blood-brain barrier, and having low toxicity.

Cannabis sativa contains more than 400 chemicals and approximately 120 cannabinoids, the active constituents of cannabis, including tetrahydrocannabinol (THC), cannabidiol (CBD), cannabinol (CBN), tetrahydrocannabivarin (THCV) and cannabigerol (CBG). Pharmacologically, the principal psychoactive constituent of cannabis is tetrahydrocannabinol (THC), which is used for treating a wide range of medical conditions, including glaucoma, AIDS wasting, neuropathic pain, treatment of spasticity associated with multiple sclerosis, fibromyalgia and chemotherapy-induced nausea. THC is also effective in the treatment of allergies, inflammation, infection, depression, migraine, bipolar disorders, anxiety disorder, drug dependency and drug withdrawal syndromes.

In formulating oral tablets, various challenges are associated with obtaining a homogenous mixture where variations are avoided and a safe and convenient delivery may be obtained. Also, the general formulation of the tablets offering convenience to the user need not be compromised which is often the case if conventional delivery means are applied.

Furthermore, it is preferable that a formulation is provided that may also help in obtaining improved sensorics properties of oral cannabinoid delivery. Here, important sensorics properties include friability, texture, flavor perception, sweetness perception and off-notes associated with cannabinoids. These properties are both relevant from a convenience perspective in oral tablets, but certainly also in order to support an appropriate delivery of cannabinoids from the tablets and avoid adverse side effects of cannabinoids.

One of the challenges with oral tablets as a delivery vehicle of cannabinoids is that cannabinoids tend to be associated with off-notes during administration due to the specific physiochemical properties of the compounds. The taste masking challenge is more profound when a higher release of cannabinoids are delivered by such tablets. If off-notes are the predominant sensation during administration, convenience may be affected and even more critically, the delivery of cannabinoids may also be affected. Saliva production may be suppressed, and the delivery vehicle may not be handled correctly.

Hence, there is a need in the prior art for improved oral tablets that solve the above-referenced challenges and problems of the prior art. In particular, there is a need in the prior art for new cannabinoid platforms that support improved saliva generation, appropriate delivery of cannabinoids combined with beneficial sensorics properties.

SUMMARY OF THE INVENTION

Accordingly there is provided an oral tablet for delivery of cannabinoids to mucosal surfaces comprising a population of particles and one or more cannabinoids, the population of particles comprising a) directly compressible (DC) sugar alcohol particles and b) non-directly compressible (non-DC) sugar alcohol particles, the non-DC particles providing the tablet with a plurality of discrete non-DC areas.

Providing an oral tablet according to the invention may solve various problems of the prior art and aims at establishing an oral tablet that combines beneficial delivery properties of cannabinoids combined with advantageous sensorics properties. Additionally, the specific application of directly compressible (DC) sugar alcohol particles and non-directly compressible (non-DC) sugar alcohol particles aims at improving the delivery vehicle according to the invention.

One advantage of the invention is a surprisingly strong saliva generation compared to conventional chewable tablets and lozenges. Particularly, the plurality of non-DC areas provided in the tablet surprisingly induce a remarkable generation of saliva. Increased generation of saliva may have a huge impact on the delivery of the one or more cannabinoids. Specifically, increased generation of saliva may increase exposure of the one or more cannabinoids to mucosal surfaces and thereby contribute to an increased uptake of cannabinoids in the oral mucosa. More specifically, when increased generation of saliva is coordinated with release of the one or more cannabinoids from the tablet, an even more pronounced effect is obtained. Even more specifically, when increased generation of saliva is commenced in a short time, the one or more cannabinoids may relatively quickly be exposed to mucosal surfaces and thereby relatively quickly deliver a desired effect. Hence, a synergy between uptake of cannabinoids and increased saliva generation may be seen according to the invention.

Having a combination of non-DC particles and DC particles in the population of particles may further facilitate sufficient mechanical strength combined with stability of the tablet, disintegrability of the tablet upon chewing, and induced saliva generation upon chewing.

One unexpected advantage over the prior art is that the saliva generation is surprisingly sustained even after a user has swallowed the bulk-portion of the non-DC sugar alcohols. This sustaining of the salivation generation may be advantageous in relation to many applications of an oral tablet ranging from mouthfeel, taste, flavor perception, etc.

It is noted that in the present context, the oral tablet comprises the population of particles, whereas the population of particles comprises the directly compressible (DC) and the non-directly compressible (non-DC) sugar alcohol particles.

In the present context, the non-DC sugar alcohol particles are understood and defined by the skilled person with reference to their typical commercial trade grade.

With respect to release properties, the present invention may offer an improved release profile of cannabinoids compared to conventional oral tablets. In particular, the specific oral tablet formulation platform of the present invention may serve to provide improved release characteristics of cannabinoids compared to conventional oral tablet formulation platforms applied in combination with cannabinoids.

A very important aspect of the present invention is the provision of beneficial sensorics properties. Here, important sensorics properties include mouthfeel, friability, texture, flavor perception, sweetness perception and off-notes associated with cannabinoids. These properties are both relevant from a convenience perspective in oral tablets, but certainly also in order to support an appropriate delivery of cannabinoids from the oral tablet formulation, such as an improved release profile, and to avoid adverse side effects of cannabinoids.

The present inventors have shown very surprising results with the specific combination of features of the present invention in terms of these sensorics properties. It was an unexpected result that the invention could both contribute to an improved release profile, such as rapid release of cannabinoids, and at the same time provide very beneficial sensorics properties which in terms may also support an appropriate delivery of cannabinoids from the oral tablet and avoid adverse side effects of cannabinoids.

One of the sensorics properties that are particularly advantageous is friability of the oral tablet. Both in order to secure a desired release of cannabinoids and to improve the sensation by a consumer, it is critical that friability is balanced. Also, the mouthfeel of the oral tablet during use is critical for the release of cannabinoids and the experience as well as convenience during use. These properties may be improved by the present invention which was not expected by the inventors of the present invention.

Advantageously, the oral tablets of the present invention can be formulated in much smaller oral tablets than traditional cannabinoid containing oral tablets and, thus, may have reduced dissolution times in the oral cavity while still achieving significant cannabinoid plasma level and obtaining comparable cannabinoid pharmacokinetic profiles to the traditional oral tablets. By reducing dissolution time and improving the speed of cannabinoid absorption, patient compliance may also be improved.

In an embodiment of the invention, the non-DC sugar alcohol particles have not been granulated prior to tableting.

Thus, the non-DC sugar alcohol particles are provided as non-granulated particles.

These are typically available in a non-DC form of the relevant sugar alcohol as particles which have not been preprocessed by granulation with other sugar alcohols or binders for the purpose of obtaining so-called direct compressible particles (DC) on the basis of sugar alcohol particles which are by themselves not suitable for direct compression. Such non-DC particles of sugar alcohol may typically consist of the sugar alcohol. Therefore, non-DC sugar alcohol particles may typically be particles consisting of sugar alcohol, which is non-directly compressible in its pure form. Examples of sugar alcohols which are non-directly compressible when provided as particles consisting of the sugar alcohol in question include erythritol, xylitol, maltitol, mannitol, lactitol, isomalt, etc.

Therefore, preferred non-DC grades of sugar alcohol may include pure sugar alcohol particles.

In an embodiment of the invention, the tablet is a chewable tablet.

In context of the present invention, a "chewable tablet" is intended to mean an oral tablet that is chewed upon oral administration, having characteristics allowing convenient chewing without adverse side effects associated with the texture of the oral tablet.

In an embodiment of the invention, at least 10% by weight of said population of particles have a particle size below 250 μm, and wherein at least 30% by weight of said population of particles have a particle size above 500 μm. In an embodiment of the invention, at least 10% by weight of said population of particles have a particle size below 250 μm, and at least 30% by weight of said non-DC sugar alcohol particles have a particle size above 500 μm.

This embodiment was shown to provide a particularly impressive generation of saliva. Without being bound by theory, it is believed that the effect is a result of more pronounced discrete areas of non-DC sugar alcohol particles in the tablet. Combined with smaller particles of DC sugar alcohol, the salivation effect was seen to be even more pronounced.

According to an embodiment of the invention, the population of particles have a particle size distribution with a full width at half maximum (FWHM) of at least 100 μm.

Particularly when having a broad particle size distribution of the population of particles, it was surprising to the inventors that even distribution of the non-DC areas could be accomplished. Typically, when having a broad particle size distribution, such as when having a width from the 10% quantile to the 90% quantile greater than 30% of the mean value, associated compositions are considered vulnerable to segregation. However, according to an embodiment of the invention, the non-DC areas are evenly distributed in at least one module of the tablet and may have amounts of non-DC particles between a series of at least 10 of the tablets holding a relative standard deviation (RSD) below 10%.

According to an embodiment of the invention, the non-DC particles have an average non-DC particle size at least 50 μm larger than an average DC particle size of the DC particles.

In an embodiment of the invention, a series of at least 10 of said tablets comprises said non-DC particles in an amount varying with a relative standard deviation (RSD) below 10%.

One advantage of the above embodiment may be that a uniform product may be obtained having low variation in the amount of non-DC sugar alcohol between tablets.

Consequently, the functionality provided by non-DC areas in the tablet may provide low variation between tablets.

It is noted that the reference to RSD and a sequence of tablets typically refers to a tablet series of a production line.

Furthermore, the RSD of the non-DC sugar alcohol between tablets is a measure of the degree of even distribution of the non-DC areas. Therefore, having an RSD below 10% in a series of at least 10 tablets indicates an even distribution of the non-DC areas. Having evenly distributed non-DC areas facilitates a high salivation since the non-DC areas are effectively distributed in the mouth upon mastication and a resulting disintegration of the tablet.

According to an embodiment of the invention, the amount of non-DC particles between a series of at least 10 of the tablets holds a relative standard deviation (RSD) below 5%.

An advantageous method of dosing non-DC sugar alcohols into a composition for a large number of tablets has been established, which facilitates an exact dosing of the non-DC sugar alcohols in a series of tablets. This means that large-scale production of tablets comprising non-DC sugar alcohols is made possible with improved results concerning distribution of the non-DC areas in the tablets and thereby an improved RSD between the tablets of a series.

The term RSD as used herein is short for the relative standard deviation, which within this present field is used to indicate the uniformity in content of non-DC sugar alcohols in a series of tablets. An analysis may be carried out on an array of 10 tablets of a series, wherein the content of the non-DC sugar alcohols in question is measured. From these values the RSD may be calculated through the standard formula of RSD=(standard deviation of array X)*100%/(average of array X).

In some cases, it may be most convenient to measure RSD of the amount of non-DC sugar alcohol particles indirectly. For example, the RSD of another ingredient may be used as an indicator for the amount of non-DC sugar alcohol particles, as segregation affects the whole composition of the tablet or module in question.

When attempting to obtain a high degree of even distribution of the non-DC areas, insufficient mixing may lead to uneven distribution, such as undesirable agglomeration of particles within certain parts of the tablet. Also, even if mixing very thoroughly the ingredients, an undesirable handling of the mixture from the mixing to a tableting machine may lead to segregation. For example, smaller particles may typically segregate to the bottom part of a container, thereby leading to different particle distributions for different tablets. Particularly when the different ingredients have different particle sizes, e.g. if non-DC particles have a larger particle size compared to other ingredients, segregation may lead to different contents of non-DC sugar alcohols in different tablets. Yet, another aspect is that even storing a thoroughly mixed composition for too long may lead to segregation.

On the other hand, a measure of having obtained even distribution of non-DC areas in at least one module of the tablet may be that a series of at least 10 of the tablets holds a relative standard deviation (RSD) below 10% with respect to the non-DC sugar alcohol content.

In is noted that the term segregation as used herein would be known to the skilled person to mean the separation of a mixture according to similarity, typically size. This may in the present context be a problem when handling a mixture comprising very different sizes of particles, e.g. in a hopper for holding and feeding the composition via a feeding mechanism to a die cavity.

In an embodiment of the invention, the non-DC areas are homogenously distributed in the tablet or at least one module of the tablet.

One advantage of the above embodiment may be that the homogenous distribution of the non-DC areas promotes an effective disintegration of the module upon mastication, e.g. due to lower mechanical strength contribution from the non-DC particles, thereby facilitating effective contacting of the resulting mastication fragments formed by the mastication with saliva, again increasing dissolving of the tablet. Also, the homogenous distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the homogenous distribution to facilitate effect dispersion of mastication fragments in the oral cavity upon mastication.

In some embodiments of the invention, the unit weight of the oral tablet is from about 200 mg to about 2000 mg.

In an embodiment of the invention, the one or more cannabinoids are present in an amount of 0.1 to 400 mg.

In an embodiment of the invention, the one or more cannabinoids are present in an amount of 10 to 100 mg.

In an embodiment of the invention, the one or more cannabinoids are present in an amount of 0.1 to 200 mg. In some other embodiments of the invention, the one or more cannabinoids are present in an amount of 0.1 to 100 mg. In some other embodiments of the invention, the one or more cannabinoids are present in an amount of 0.1 to 50 mg. In an embodiment of the invention said oral tablet comprises said cannabinoids in an amount of 0.1-30 mg, such as 1-20 mg, such as 5-15 mg.

In an embodiment of the invention, the one or more cannabinoids comprise cannabidiol (CBD), cannabidiolic acid (CBDA), cannabidivarin (CBDV), salts and derivatives thereof.

In an embodiment of the invention, the one or more cannabinoids comprise tetrahydrocannabinol (THC), tetrahydrocannabinolic acid (THCA), tetrahydrocannabivarin (THCV), salts and derivatives thereof.

In an embodiment of the invention, the one or more cannabinoids comprise cannabigerol (CBG), salts and derivatives thereof.

In some embodiments of the invention, the cannabinoid is selected from the group consisting of cannabidiol (CBD), cannabidiolic acid (CBDA), tetrahydrocannabinol (THC), tetrahydrocannabinolic acid (THCA), cannabigerol (CBG), cannabichromene (CBC), cannabinol (CBN), cannabielsoin (CBE), iso-tetrahydrocannabinol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV), cannabigerol monomethyl ether (CBGM), salts thereof, derivatives thereof and mixtures of cannabinoids.

In an embodiment of the invention, the one or more cannabinoids comprise cannabidiol (CBD), cannabidiolic acid (CBDA), cannabidivarin (CBDV), salts and derivatives thereof. In an embodiment of the invention the one or more cannabinoids comprises CBD, salts and derivatives thereof, including analogues and homologues. In an embodiment of the invention said one or more cannabinoids comprises CBD. In an embodiment of the invention said one or more cannabinoids is CBD.

In an embodiment of the invention, the one or more cannabinoids comprise tetrahydrocannabinol (THC), tetrahydrocannabinolic acid (THCA), tetrahydrocannabivarin (THCV), salts and derivatives thereof. In an embodiment of the invention said one or more cannabinoids comprises tetrahydrocannabinol (THC). Preferably THC is intended to mean (⁻)-trans-$\Delta^9$-tetrahydrocannabinol, i.e. (6aR,10aR)-delta-9-tetrahydrocannabinol). In an embodiment of the invention said one or more cannabinoids is THC.

In an embodiment of the invention, wherein the one or more cannabinoids comprise at least two cannabinoids. In an embodiment of the invention said one or more cannabinoids comprises a combination of several cannabinoids, such as THC and CBD. In an embodiment of the invention said one or more cannabinoids is a combination of THC and CBD.

In an embodiment of the invention, the non-DC sugar alcohol particles are selected from non-DC particles of erythritol, maltitol, xylitol, isomalt, lactitol, mannitol, and combinations thereof.

One advantage of the above embodiment may be that a desirable induced saliva generation is obtained.

According to an embodiment of the invention, the non-DC sugar alcohol particles consist of sugar alcohols selected from erythritol, maltitol, xylitol, isomalt, lactitol, mannitol, and combinations thereof.

In an embodiment of the invention, the non-DC sugar alcohol particles are selected from non-DC particles of erythritol, maltitol, xylitol, isomalt, and combinations thereof.

One advantage of the above embodiment may be that a desirable induced saliva generation is obtained.

In an embodiment of the invention, the non-DC sugar alcohol particles are selected from non-DC particles of erythritol, maltitol, xylitol, and combinations thereof.

In an embodiment of the invention, the non-DC sugar alcohol particles are non-DC erythritol particles.

One advantage of the above embodiment may be that a desirable induced saliva generation is obtained, together with a cooling sensation.

In an embodiment of the invention, the non-DC sugar alcohol particles are non-DC xylitol particles.

One advantage of the above embodiment may be that a desirable induced saliva generation is obtained, together with a cooling sensation.

In an embodiment of the invention, the tablet comprises said non-DC sugar alcohol particles in an amount of at least 10% by weight of the tablet.

In an embodiment of the invention, said DC sugar alcohol particles comprises sugar alcohols selected from DC particles of sorbitol, erythritol, xylitol, lactitol, maltitol, mannitol, isomalt, and combinations thereof.

Sorbitol is an example of a sugar alcohol, which is considered DC grade, when provided as particles consisting of sorbitol, i.e. in its pure form. On the other hand, several other sugar alcohols are considered non-DC grade if providing them as particles consisting of the specific sugar alcohol. Therefore, such non-DC sugar alcohols are conventionally processed into DC grade sugar alcohols, e.g. by granulating them with e.g. a binder.

Examples of trade grades of DC sugar alcohols include sorbitol particles provided as e.g. Neosorb® P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab 200 from Dupont.

In an embodiment of the invention, the tablet comprises said DC sugar alcohol particles in an amount of at least 10% by weight of the tablet.

According to an embodiment of the invention, said population of particles comprises DC sugar alcohol particles in an amount of at least 10% by weight.

In an embodiment of the invention, the tablet has a weight ratio between said non-DC sugar alcohol particles and said DC sugar alcohol particles, which is between 0.3 and 0.7.

The weight ratio between non-DC sugar alcohol particles and DC sugar alcohol particles have proven significant according to an embodiment of the invention in the sense that a relatively high amount of non-DC sugar alcohol particles must be present in order to obtain the mouthfeel and taste obtained through the invention. However, this taste and mouthfeel also resides in the DC sugar alcohol particles. An example of such DC sugar alcohol particle is DC grade xylitol, which, together with the non-DC sugar alcohol particles may provide a mouthfeel which is unique and very attractive to test panels.

The weight ratio between non-DC sugar alcohol particles and DC sugar alcohol particles have proven significant as mentioned above in relation to the direct sensation and mouthfeel experienced by the user but is has moreover addressed the challenge in relation to mouthfeel when DC sugar alcohol particles crumbles during the initial chew. The mechanical stability of the tablet is much desired when the tablet is in its non-chewed form, but a fast disintegration and dissolving is desirable when the tablet is chewed due to the fact that user of the tablet dislike a sandy mouthfeel induced through small hard-pressed crumbles of DC sugar alcohol. The use of a very high amount of non-DC sugar alcohol particles will facilitate a perceived fast dissolving and disintegration of the tablet after the initial chews.

According to an embodiment of the invention the tablet has a weight ratio between said non-DC sugar alcohol particles and said DC sugar alcohol particles, which is greater than 0.3, such as greater than 0.4, such as greater than 0.5.

According to an embodiment of the invention the tablet has a weight ratio between said non-DC sugar alcohol particles and said DC sugar alcohol particles, which is smaller than 0.7, such as smaller than 0.6, such as smaller than 0.55.

The weight ratio between non-DC sugar alcohol particles and DC sugar alcohol particles is important for the purpose of obtaining an advantageous taste and mouthfeel. By having an upper limit of this weight ratio, the chewer will moreover also experience a desirable crunch sensation when masticating the tablet, the crunch being obtained through the use of substantial amounts of DC sugar alcohol particles and the non-DC sugar alcohol particles.

According to an embodiment of the invention, the tablet comprises the non-DC sugar alcohol particles in an amount of greater than 0.3 gram.

According to an embodiment of the invention, the weight of non-DC sugar alcohol particles contained in the tablet is greater than greater than 0.4 gram, such as greater than 0.5 gram, such as greater than 0.6 gram, such as greater than 0.7 gram, such as greater than 0.8 gram, such as greater than 0.9 gram, such as greater than 1.0 gram.

According to a further embodiment of the invention, the amount of non-DC sugar alcohol particles is relatively high. It is in particular high when considering that the non-DC sugar alcohol in conventional sense is not regarded attractive for compression, but the mouthfeel and salivation perceived by the user is there improved significantly, when compared to low amounts or the same amounts of DC sugar alcohol.

According to an embodiment of the invention, the tablet comprises the non-DC sugar alcohol particles in an amount of less than 3.0 gram, such as less than 2.0 gram, such as less than 1.5 gram.

In an embodiment of the invention wherein the tablet has a weight of between 0.5 and 4.0 grams.

In an embodiment of the invention, the non-DC areas result in induced saliva generation upon mastication of the tablet.

In an embodiment of the invention, saliva generation upon mastication of the tablet is induced compared to a tablet without non-DC sugar alcohol particles.

In an embodiment of the invention, saliva generation upon mastication of the tablet is induced compared to a tablet where the discrete areas are based on DC sugar alcohol particles.

In an embodiment of the invention, the tablet generates more than 1.5 mL saliva within 30 seconds from onset of mastication.

According to an embodiment of the invention the discrete non-DC areas induces saliva generation of more than 2.0 mL saliva within 30 seconds from onset of mastication.

According to an embodiment of the invention the discrete non-DC areas induces saliva generation of more than 3.0 mL saliva within 30 seconds from onset of mastication.

In an embodiment of the invention, the tablet generates more than 1.5 mL saliva within a period from 30 to 90 seconds from onset of mastication.

According to an embodiment of the invention the discrete non-DC areas induces saliva generation of more than 2.0 mL saliva within 30 to 90 seconds from onset of mastication.

In an embodiment of the invention, the tablet generates more than 1.5 mL saliva within a period from 90 to 180 seconds from onset of mastication.

In an embodiment of the invention, the tablet generates more than 1.5 mL saliva within a period from 180 to 300 seconds from onset of mastication.

In an embodiment of the invention, the tablet comprises a self-emulsifying system that when hydrated with saliva upon oral administration forms an emulsion for delivery of the one or more cannabinoids to a mucosal surface.

Due to the poor solubility of cannabinoids in physiological fluids, it is also an unmet need to have a high dose of cannabinoid in a form, that solubilize the cannabinoids upon mixture with the body physiological fluids to facilitate bio-absorption. To overcome low oral bioavailability, various lipid-based drug delivery systems and self-emulsifying systems have been developed. Lipid-based delivery systems and particularly self-emulsifying drug delivery systems (SEDDS) have been demonstrated to increase the solubility, dissolution and bioavailability of many insoluble drugs. However, lipid-based and SEDDS delivery systems are also very limited by the amount of drug loading that has to be dissolved in the vehicle composition. Higher concentration of active ingredients are obtained using co-solvents, which enable drug loads of up to 30% in specific cases.

Particular challenges is considered to arise in formulating oral tablets with cannabinoid delivery systems, such as SEDDS or cyclodextrin complexes. For instance, challenges may arise with obtaining a homogenous mixture where variations are avoided and a safe and convenient delivery may be obtained. Also, the general formulation of the oral tablets offering convenience to the user need not be compromised which is often the case if precaution is not taken, such as in cases where a high cannabinoid load is needed.

Particularly with respect to SEDDS, the formulation of the present invention may provide some clear benefits, both allowing a higher load of cannabinoids and at the same time offer improved sensorics properties of the formulation during use. Other advantages are also present.

Importantly, the presence of SEDDS or at least a self-emulsifying agent was seen to act in synergy with increased saliva generation. While increased saliva generation was seen to distribute cannabinoids and allocate a higher load of cannabinoids to the mucosal surfaces, the presence of SEDDS or at least a self-emulsifying agent was seen to further increase the uptake of the one or more cannabinoids through oral surfaces. Accordingly, the synergy between the presence of SEDDS or at least a self-emulsifying agent and increased saliva generation according to the invention was a surprise to the inventors. In some embodiments, increased saliva generation may result in a higher exposure of the one or more cannabinoids to mucosal surfaces. The presence of SEDDS may work to increase the affinity of the one or more cannabinoids from this saliva to the mucosa. Particularly, the potential of SEDDS to have a high load of cannabinoids further contributes to the synergy of the tablet according to the invention in combination with improved saliva generation.

In the present context, SEDDS is a solid or liquid dosage form comprising an oil phase, a surfactant and optionally a co-surfactant, characterized primarily in that said dosage form can form oil-in-water emulsion spontaneously in the oral cavity or at ambient temperature (referring generally to body temperature, namely 37° C.). When a SEDDS enters the oral cavity, it is initially self-emulsified as emulsion droplets and rapidly dispersed throughout the oral cavity, and thus reducing the irritation caused by the direct contact of the drug with the mucous membrane of the oral cavity. In the oral cavity, the structure of the emulsion microparticulate will be changed or destroyed. The resulting microparticulate of micrometer or nanometer level can penetrate into the mucous membrane of the oral cavity, and the absorbed oil droplets enter the blood circulation, thereby significantly improving the bioavailability of the drug.

In an embodiment of the invention, the self-emulsifying system comprises one or more emulsifiers and one or more oil carriers.

In an embodiment of the invention, the self-emulsifying system comprises one or more emulsifiers, one or more oil carriers and one or more solubilizers.

In an embodiment of the invention, the self-emulsifying system comprises one or more emulsifiers, one or more oil carriers, one or more solubilizers and one or more solvents.

In an embodiment of the invention, the self-emulsifying system comprises one or more emulsifiers and one or more solvents.

In an embodiment of the invention, the self-emulsifying system comprises one or more emulsifiers that have both emulsifying and solubilizing properties.

In an embodiment of the invention, the self-emulsifying system comprises one or more emulsifiers that act as both an emulsifier and a carrier.

In an embodiment of the invention, the self-emulsifying system comprises one or more emulsifiers that act as both an emulsifier, a carrier and a solubilizer.

In an embodiment of the invention, the self-emulsifying system comprises one or more fatty acids, one or more glycerols, one or more waxes, one or more flavonoids and one or more terpenes.

In an embodiment of the invention, the self-emulsifying system comprises one or more cannabinoid extracts.

In an embodiment of the invention, the self-emulsifying system comprises one or more emulsifiers that have an HLB-value of more than 6, preferably of 8-18.

In an embodiment of the invention, the one or more emulsifiers are selected from the group consisting of PEG- 35 castor oil, PEG-6 oleoyl glycerides, PEG-6 linoleoyl glycerides, PEG-8 caprylic/capric glyceride, sorbitan monolaurate, sorbitan monooleate, polyoxyethylene (20) sorbitan monolaurate, polyoxyethylene (60) sorbitan monostearate, polyoxyethylene (80) sorbitan monooleate, lauroylpoloxyl-32 glycerides, stearoyl polyoxyl-32 glycerides, polyoxyl-32 stearate, propylene glycol mono laurate, propylene glycol di laurate, and mixtures and combinations thereof.

In an embodiment of the invention, the one or more emulsifiers comprise PEG-35 castor oil.

In an embodiment of the invention, the oral tablet further comprising an emulsifier selected from the group consisting of sugar fatty acid esters, mono-glycerides, di-glycerides, diacetyl tartaric acid ester of monoglyceride, diacetyl tartaric acid esters of diglyceride, polyglycerol esters, calcium stearoyl lactylate, sodium stearoyl lactylate, and mixtures and combinations thereof.

In an embodiment of the invention, the oil carrier is selected from the group consisting of natural fatty acids; medium-chain triglycerides of caprylic (C8) and capric (C10) acids; propylene glycol esters of caprylic (C8) and capric (C10) acids; mono-, di- and triglycerides of mainly linoleic (C18:2) and oleic (C18:1) acids; fatty acid 18:1 cis-9; natural fatty acids; mono-, di- and triglycerides of oleic (C18:1) acid, and mixtures and combinations thereof.

In an embodiment of the invention, the oil carrier is selected from the group consisting of corn oil, Labrafac lipophile WL1349, Labrafac PG, Maisine CC, oleic acid, olive oil, Peceol, and mixtures and combinations thereof.

In an embodiment of the invention, the one or more solvents are selected from the group consisting of polyglyceryl-3 dioleate, 1,2-propandiol, polyethylene glycol 300, polyethylene glycol 400, diethylene glycol monoethyl ether, and mixtures and combinations thereof.

In an embodiment of the invention, the one or more solubilizers are selected from the group consisting of lauroylpoloxyl-32 glycerides; stearoyl polyoxyl-32 glycerides; Polyoxyl-32 stearate; synthetic copolymer of ethylene oxide (80) and propylene oxide (27); polyvinyl caprolactam-polyvinyl acetate-polyethylene glycol graft co-polymer; alpha-, beta- or gamma cyclodextrins and derivatives thereof; pea proteins (globulins, albumins, glutelins proteins); and mixtures and combinations thereof.

In an embodiment of the invention, the one or more cannabinoids are present in a premixture.

In an embodiment of the invention, the one or more cannabinoids are present in a premixture and reversibly adsorbed onto one or more solid particles.

In the present context, a "premixture" is intended to mean that the one or more cannabinoids have been mixed with the one or more solid particles prior to being applied in the oral tablet together with the additional tablet components.

In the present context, a premixture is partly used to allocate the one or more cannabinoids properly to the manufacturing process and secure that the uniformity is not compromised and that the cannabinoids are distributed properly into the mixture. Preferably, the cannabinoids are provided in a premixture with one or more sugar alcohols. It was a surprise to the inventors that a premixture was important to have in order for the cannabinoids be to distributed properly in the manufacturing process and to end up with a product where the uniformity was consistent.

In an embodiment of the invention, the one or more cannabinoids are present in a premixture and reversibly adsorbed onto one or more solid particles, the one or more cannabinoids applied by means of spraying.

In an embodiment of the invention, the one or more cannabinoids are present in a premixture and reversibly adsorbed onto one or more solid particles, the one or more cannabinoids applied by means of a thin layer to the surface of the one or more solid particles.

In an embodiment of the invention, the premixture is present in an amount of 5 to 50% by weight of the tablet.

In some embodiments of the invention, the weight ratio of the one or more cannabinoids relative to the one or more solid particles is from 1:30 to 1:1.

In some embodiments of the invention, the weight ratio of the one or more cannabinoids relative to the one or more solid particles is from 1:25 to 1:5.

In some embodiments of the invention, the weight ratio of the one or more cannabinoids relative to the one or more solid particles is from 1:20 to 1:10.

In some embodiments of the invention, the plurality of solid particles are present in an amount of at least 5% by weight of the tablet.

In some embodiments of the invention, the plurality of solid particles are present in an amount of at least 10% by weight of the composition.

In some embodiments of the invention, the plurality of solid particles are present in an amount of at least 20% by weight of the composition.

In some embodiments of the invention, the plurality of solid particles are present in an amount of at most 30% by weight of the composition.

In some embodiments of the invention, the plurality of solid particles comprise microcrystalline cellulose.

In some embodiments of the invention, the plurality of solid particles are selected from the group consisting of silica, microcrystalline cellulose, cellulose, silicified microcrystalline cellulose, clay, talc, starch, pregelatinized starch, calcium carbonate, dicalcium phosphate, magnesium carbonate, magnesium-alumino-metasilicates, hyper porous silica and mixtures thereof.

In some embodiments of the invention, the plurality of solid particles comprise one or more sugar alcohols.

In some embodiments of the invention, the one or more solid particles are selected from the group consisting of xylitol, lactitol, sorbitol, maltitol, erythritol, isomalt and mannitol, and mixtures and combinations thereof.

In some embodiments of the invention, said population of particles is comprised in a first module of the tablet and a second population of particles is comprised in a second module of the tablet.

Thus, a synergy between utilization of non-DC sugar alcohol particles as a disintegration promoter due to the lower mechanical strength and also as a salivation promoter in combination with a second module, which can provide additional mechanical strength, thereby acting as a carrier module. This is especially advantageous when the second population of particles contributes to an attractive mouthfeel by a high content of DC sugar alcohols, which also provides mechanical strength to the tablet.

One advantage of the above embodiment may be that the second module may have a higher mechanical strength, e.g. by means of a different composition comprising e.g. a very large amount of direct compressible ingredients, such as DC sugar alcohols.

A further advantage of the above embodiment may be that the second module may have a higher loading capacity for e.g. cannabinoids, partly due to the higher obtainable mechanical strength achievable by large amounts of direct compressible ingredients, such as DC sugar alcohols.

Thus, in the above embodiment said population of particles is tabletted into a first module, and wherein the tablet further comprises a second population of particles that is tabletted into a second module. The first module may be tabletted before the second module, or vice versa. In some embodiments, the tablet may comprise one or more further modules.

In an embodiment of the invention, the oral tablet comprises at least two modules. A tablet comprising two or more modules will have module sizes which each are comparable to the volume of the complete tablet. Comparable in the present context means that the modules are not understood as small particles and a module should at least be greater than 1/20 of the complete tablet volume, preferably greater than 1/10 of the complete tablet volume.

The module may typically be gathered from a plurality of compressed particles and have a weight which is greater than 0.2 gram and less than 10 grams.

In an embodiment of the invention, a module is defined as a plurality of particles being compressed together to form a gathered module of particles.

In an embodiment of the invention, the oral tablet comprises a plurality of oral tablet modules. In the present context the application of e.g. two modules are in particular advantageous as the use of non-DC sugar alcohols by nature may result in a more fragile tablet or at least the module in which the non-DC sugar alcohols are. In other words, non-DC sugar alcohols may be present primarily in one module thereby optimizing the desired salivation and sensory experience from the module and the tablet as such whereas another module may serve as a support ensuring that the desired stability and friability of the complete tablet is obtained.

In an embodiment of the invention, the plurality of modules are slice-like layers. The term "slice-like" layer is a plain but very precise way of to the skilled person how a module may be provided, as such a layer is a standard structure obtained through conventional tabletting procedures.

According to an embodiment of the invention, the tablet has two modules. Optionally, a coating may be applied around the two modules to form the final tablet.

An advantage of using two modules is described above, but it should also be noted that this effect may also be obtained when applying layers of very different nature.

Such application may e.g. include the use of a gum module and a non-gum module, where the non-gum modules are containing the non-DC sugar alcohol particles. In this way, the non-gum layer may release the advantageous non-DC sugar alcohols and the gum layer may both stabilize the tablet as described above but also interact with the non-DC sugar alcohols during in particular the initial release for establishment of a very pleasant and impressing initial chew phase. This includes an increased saliva and moisture experience.

In an embodiment of the invention said population of particles is tabletted into a first module and combined with a second population of particles that is tabletted into a second module, where the second population of particles is different from the first population of particles.

In an embodiment of the invention said population of particles is tabletted into a first module and combined with a second population of particles that is tabletted into a second module, where the second population of particles is different from the first population of particles, where the second population of particles is free of non-DC sugar alcohols.

In one embodiment, the second population of particles comprises a large amount of DC sugar alcohols, such as larger amounts than the first population of particles. For example, the second population of particles may comprise at least 30% by weight of DC sugar alcohols, such as at least 50% by weight of DC sugar alcohols, such as at least 70% by weight of sugar alcohols. In an example embodiment, the second population of particles may comprise between 50 and 99.9% by weight of sugar alcohols, such as between 70 and 99% by weight of sugar alcohols.

In an embodiment of the invention the second module is tabletted before the first module.

In an embodiment of the invention, the non-DC areas are evenly distributed in the tablet or at least one module of the tablet.

One advantage of the above embodiment may be that the even distribution of the non-DC areas promotes an effective disintegration of the module upon mastication, e.g. due to lower mechanical strength contribution from the non-DC particles, thereby facilitating effective contacting of the resulting mastication fragments formed by the mastication with saliva, again increasing dissolving of the tablet. Also, the even distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the even distribution to facilitate effect dispersion of mastication fragments in the oral cavity upon mastication.

According to an embodiment of the invention, the first module comprises DC sugar alcohol particles in an amount of at least 10% by weight.

In an embodiment of the invention, the second module comprises DC sugar alcohol particles in an amount of at least 30% by weight of the second module In an embodiment of the invention, the second module comprises DC sugar alcohol particles in an amount of at least 50% by weight of the second module.

In an embodiment of the invention, the DC sugar alcohol particles in the second module are selected from DC particles of sorbitol, erythritol, xylitol, lactitol, maltitol, mannitol, isomalt, and combinations thereof.

In an embodiment of the invention, the friability of the tablet is less than 3%, such as less than 2%, such as less than 1.5%, wherein friability is measured according to European Pharmacopoeia 9.1, test method 2.9.7. by using a pharmaceutical friability-tester PTF 10E from Pharma Test.

One advantage of the above embodiment may be that a tablet with a relatively high mechanical stability is obtained, while at the same time having the desirable mouthfeel of the invention.

According to an embodiment of the invention, friability of the tablet is between 0.2% and 3%, such as between 0.2% and 2%, wherein friability is measured according to European Pharmacopoeia 9.1, test method 2.9.7. by using a pharmaceutical friability-tester PTF 10E from Pharma Test.

In an embodiment of the invention, the tablet comprises one or more binders other than binders forming part of the DC sugar alcohol particles in an amount of 0.1 to 6% by weight of the tablet.

Suitable binders include Gum Arabic, Methyl Cellulose, Liquid glucose, Tragacanth, Ethyl Cellulose, Gelatin, Hydroxy Propyl Methyl Cellulose (HPMC), Starches, Hydroxy Propyl Cellulose (HPC), Pregelatinized Starch, Sodium Carboxy Methyl Cellulose (NaCMC), Alginic Acid, Polyvinyl Pyrrolidone (PVP), Maltodextrine (MD); Cellulose, Polyethylene Glycol (PEG), Polyvinyl Alcohols, Polymethacrylates, Copovidone or Microcrystalline Cellulose (MCC), alone or in combination.

According to an embodiment of the invention, the one or more binders comprises one or more cellulose binders.

In an embodiment of the invention the one or more binders comprises microcrystalline cellulose (MCC), hydroxypropyl cellulose (HPC) or hydroxypropylmethyl cellulose (HPMC) or any combination thereof.

In an embodiment of the invention the oral tablet comprises hydroxypropyl cellulose (HPC) binder in the amount of 0.1 to 6% by weight of the tablet, such as 0.1 to 5%, such as 0.1 to 4%, such as 0.1 to 3%, such as 0.1 to 2% by weight of the tablet.

HPC may be applied as a particular attractive binder. Thus, this binder, when used with non-DC sugar alcohols such as erythritol, exhibits an advantageous sensory experience when compared to other well-known binders. In particular, the user of HPC lower than 4% by weight of the tablet is advantageous, such as 0.1 to 3%, such as 0.1 to 2% by weight of the tablet.

In an embodiment of the invention, the non-DC sugar alcohol particles are particles that are not granulated, and the one or more binders are present as separate components in the tablet.

In an embodiment of the invention, the non-DC sugar alcohol particles are particles consisting of the sugar alcohol and the particles are not pre-granulated together with the one or more binders that are present in the tablet as separate components. It is noted that the use of binders as particles separate from the non-DC particles does not compromise the advantageous sensory properties even when applying a firm pressure tableting force, whereas the granulation with the binder to the sugar alcohol clearly reduces the desired sensory properties.

In an embodiment of the invention, the resistance to crunching of the tablet is greater than 60N, such as greater than 70N, such as greater than 80N, such as greater than 90N, such as greater than 100 N, such as greater than 110, such as greater than 130N such as greater than 150N, wherein the resistance to crunching of the tablet is less than 300N, such as less than 250N, such as less than 200N, wherein the resistance to crunching is determined according to European Pharmacopoeia 9.1, test method 2.9.8. by using a pharmaceutical resistance to crunching tester model Pharma Test type PTB 311.

According to an embodiment of the invention, the tablet comprises at least one module, the module comprising more than 10% by weight of compressed non-DC sugar alcohol particles, the resistance to crunching of the module being greater than 60N, such as greater than 70N, such as greater than 80N, such as greater than 90N such as greater than 100 N, where the resistance to crunching is determined according to the European Pharmacopoeia 9.1, test method 2.9.8. by using a pharmaceutical resistance to crunching tester model Pharma Test type PTB 311.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the formulation.

In an embodiment of the invention, the tablet comprises flavor.

The amount of flavor may e.g. be from 0.1 to about 10% by weight of the tablet, such as 0.1 to about 6% by weight of the tablet.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), chili, cinnamon redhots, cotton candy, circus cotton candy, clove, coconut, coffee, clear coffee, double chocolate, energy cow, ginger, glutamate, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

According to an embodiment of the invention, the one or more cannabinoids are included in the population of particles.

In an embodiment of the invention, the oral tablet comprises gum base, and wherein the tablet is designed to be masticated into a coherent residual containing water-insoluble components.

The application of gum base may in the present context invoke a delay of the release of the one or more cannabinoids and this may again promote the buccal absorption of one or more cannabinoids when these are released from the oral tablet during mastication.

In an embodiment of the invention, the oral tablet comprises gum base, and wherein the gum base comprises at least 5% by weight of elastomer.

The specific use of a relatively high proportion of elastomer in the gum base may effectively be used for modification of the release of the one or more cannabinoids in terms of time and amount and the elastomer may also provide robust structure of the tablet facilitating that it is chewed into a coherent residual containing water-insoluble components.

In an embodiment of the invention, the gum base comprises at least 10% by weight of elastomer.

In an embodiment of the invention the gum base comprises at least 15% by weight of elastomer.

In an embodiment of the invention the gum base comprises between 15% and 25% by weight of elastomer.

In an embodiment of the invention the gum base comprises between 17% and 23% by weight of elastomer.

In an embodiment of the invention, the elastomer is selected from styrene-butadiene rubber (SBR), butyl rubber, polyisobutylene (PIB), and combinations thereof.

In an advantageous embodiment of the invention, said population of particles is tableted into a first module and combined with a second population of particles that is tableted into a second module.

In an advantageous embodiment of the invention, the tablet comprises c) particles comprising gum base.

In an advantageous embodiment of the invention a) and b) is comprised in a first module and c) is comprised in a second module.

Thus, the oral tablet comprises a first module and a second module, the first module comprising a) DC sugar alcohol particles and b) non-DC sugar alcohol particles, the second module comprising c) particles comprising gum base.

In an advantageous embodiment of the invention a) and b) is tableted into a first module and c) is tableted into a second module, wherein the first module is free of gum base.

Thus, a) DC sugar alcohol particles and b) non-DC sugar alcohol particles are tableted into a first, gum base free module whereas and c) particles comprising gum base are tableted into a second module. The second module may or may not comprise DC sugar alcohol particles and/or non-DC sugar alcohol particles.

In an advantageous embodiment of the invention, a) and b) is tableted into a first module and c) is tableted into a second module.

In an embodiment of the invention, the particles comprising gum base have an average particle size of at least 400 μm, such as between 400 μm and 1400 μm.

According to an embodiment of the invention, the particles comprising gum base consists of gum base. When the gum base particles consist of gum base, they typically have an average particle size between 800 μm and 1400 μm.

In an embodiment of the invention, the tablet comprises at least 20% by weight of gum base.

In an embodiment of the invention the oral tablet comprises between 20% and 60% by weight of gum base.

In an embodiment of the invention, the gum base comprises at least 5% by weight of resins.

According to an advantageous embodiment of the invention, the gum base comprises at least 10% by weight of resins, such as at least 15% by weight of resins, such as at least 20% by weight of resins.

According to a further advantageous embodiment of the invention, the gum base comprises at least 30% by weight of resins, such as at least 40% by weight of resins, such as at least 45% by weight of resins.

In an advantageous embodiment, the content of resin is from 40-60% by weight of the gum base.

In an embodiment of the invention, the gum resins are selected from natural resins and/or synthetic resins including low molecular weight polyvinyl acetate (PVA).

In an embodiment of the invention, the gum resins are selected from the natural resins and/or synthetic resins.

In an embodiment of the invention, the particles comprising gum base comprises gum base in an amount of 20-99.9% by weight.

In an embodiment of the invention, the particles comprising gum base consists of gum base.

In an embodiment of the invention, the tablet is free of gum base.

In an embodiment of the invention, the oral tablet further comprising a binder, such as a dry or wet binder.

In an embodiment of the invention, the oral tablet further comprising at least one dissolution modifier selected from the group consisting of acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof.

In an embodiment of the invention, the at least one dissolution modifier is selected from the group consisting of sodium alginate, calcium polycarbophil, xanthan gum and mixtures thereof.

In an embodiment of the invention, the oral tablet further comprising at least one viscolising agent that when hydrated forms a gel having positive surface electrical charge and at least one viscolising agent that when hydrated forms a gel having negative surface electrical charge.

In an embodiment of the invention, the one or more cannabinoids are present in solid form. In an embodiment of the invention, the one or more cannabinoids are present in liquid or semi-liquid form.

In an embodiment of the invention, the one or more cannabinoids form part of a complex with cyclodextrin.

Additionally, with respect to complexation of one or more cannabinoids with cyclodextrin, the formulation of the present invention may provide some clear benefits, both allowing a higher load of cannabinoids and at the same time offer improved sensorics properties of the formulation during use. Other advantages are also present.

In an embodiment of the invention, the one or more cyclodextrins comprise alpha, beta or gamma cyclodextrin or derivatives thereof.

In an embodiment of the invention, the one or more cyclodextrins form a lipophilic association with the one or more cannabinoids.

In an embodiment of the invention, the one or more cyclodextrins form a complex with the one or more cannabinoids.

In an embodiment of the invention, the one or more cannabinoids comprise at least one phytocannabinoid that forms part of an extract. In some embodiments of the invention, it was seen that cannabinoids as part of an extract may enhance the release of cannabinoids.

In an embodiment of the invention, the one or more cannabinoids comprise at least one isolated cannabinoid.

In an embodiment of the invention, the one or more cannabinoids are located in a protein carrier, such as pea protein carrier.

In an embodiment of the invention, the one or more cannabinoids comprise at least one endocannabinoid or endocannabinoid-like compound, such as palmitoylethanolamide (PEA).

In an embodiment of the invention, the one or more cannabinoids comprise at least one water-soluble cannabinoid. Water-soluble cannabinoids may enhance the release according to the present invention.

In an embodiment of the invention, the one or more cannabinoids are derived from plant material.

In an embodiment of the invention, the composition does not comprise plant material.

In an embodiment of the invention, the composition comprises enzyme inhibitors or efflux inhibitors.

In an embodiment of the invention, the tablet comprises a lipophilic association between the one or more cannabinoids and a fatty acid, such as oleic acid.

In an embodiment of the invention, the composition comprises one or more antioxidants.

In an embodiment of the invention, the one or more cannabinoids have a systemic effect.

In an embodiment of the invention, the one or more cannabinoids have a local effect.

In another aspect of the invention, the oral tablet may be used for the treatment or alleviation of a medical condition.

In certain embodiments of the invention, the oral tablet of the present invention may be used for the treatment or alleviation of a medical condition selected from the group consisting of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

Moreover, the invention relates to an oral tablet with one or more cannabinoids comprising a population of particles, the population of particles comprising directly compressible (DC) and non-directly compressible (non-DC) sugar alcohol particles, the tablet being designed to turn into liquid within 20 seconds of mastication.

Moreover, the invention relates to an oral tablet with one or more cannabinoids comprising a population of particles, the population of particles comprising directly compressible (DC) and non-directly compressible (non-DC) sugar alcohol particles, the tablet being designed to dissolve within 20 seconds of mastication.

Moreover, the invention relates to a method for delivery of cannabinoids to mucosal surfaces, the method comprising the steps of: i) providing an oral delivery tablet comprising a population of particles and one or more cannabinoids, the population of particles comprising a) directly compressible (DC) sugar alcohol particles and b) non-directly compressible (non-DC) sugar alcohol particles and ii) masticating the tablet and thereby generating saliva in the oral cavity induced by a plurality of discrete non-DC areas in the tablet.

Moreover, the invention relates to a method for delivery of cannabinoids to mucosal surfaces, the method comprising the steps of: i) providing an oral delivery tablet comprising a population of particles and one or more cannabinoids, the population of particles comprising a) directly compressible (DC) sugar alcohol particles, b) non-directly compressible (non-DC) sugar alcohol particles and c) particles comprising gum base, and ii) masticating the tablet and thereby generating saliva in the oral cavity induced by a plurality of discrete non-DC areas in the tablet.

THE FIGURES

The invention will now be described with reference to the drawings where

Figure 5:
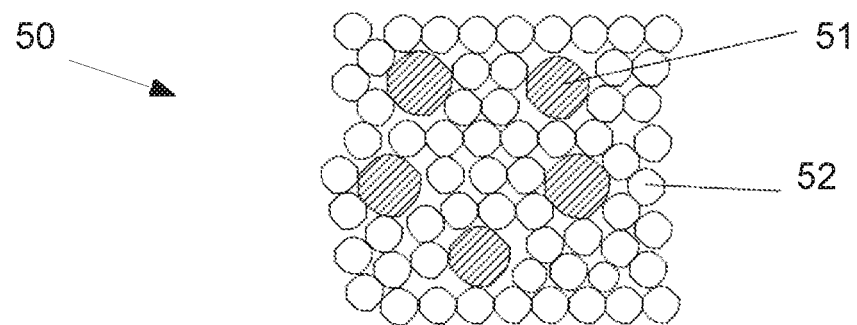
Figure 6:
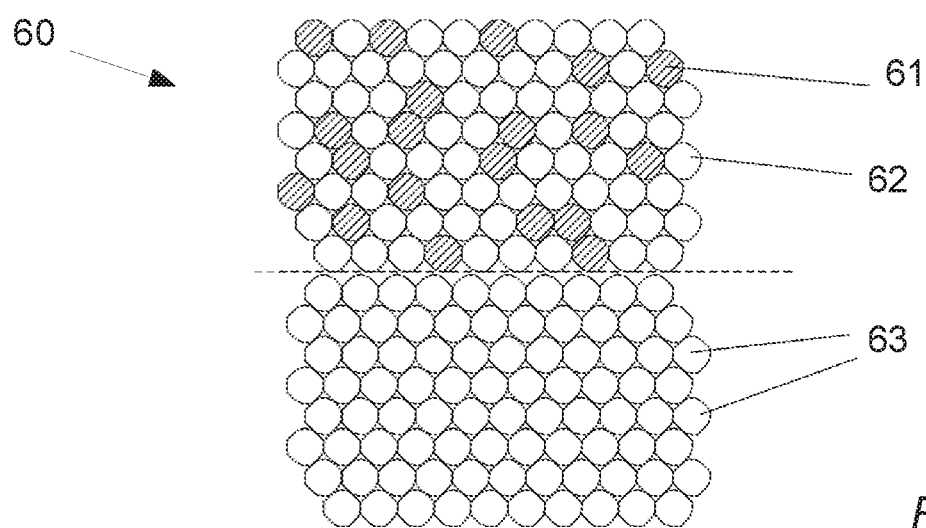
Figure 7:
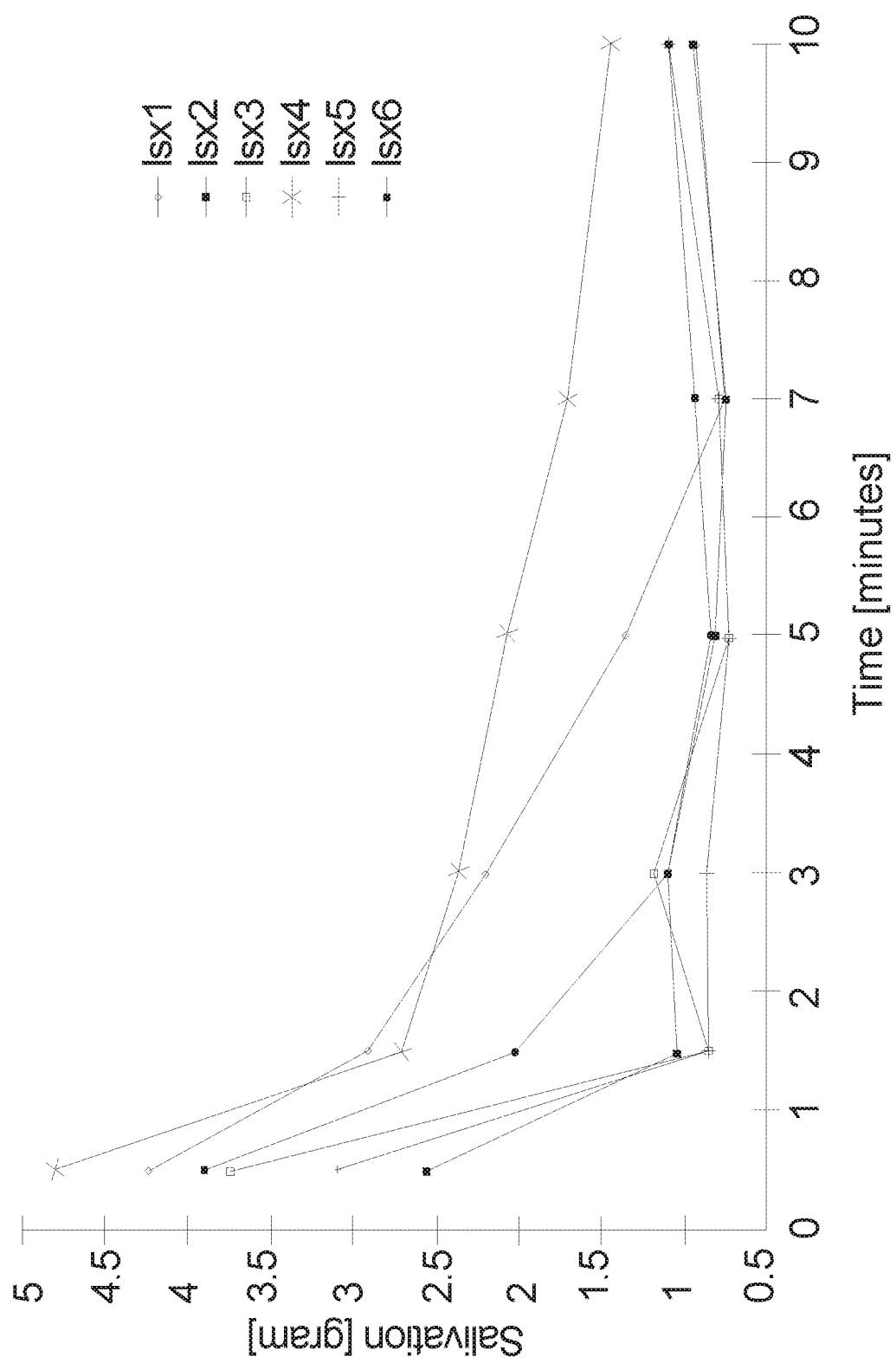

FIGS. 1a and 1b shows an embodiment of the invention,
FIGS. 2a and 2b shows a two-module version of an embodiment of the invention,
FIGS. 3a and 3b shows a three-module version of an embodiment of the invention,
FIGS. 4 and 5 illustrates embodiments of the invention
FIG. 6 illustrates a two-module version of an embodiment of the invention and where
FIG. 7 illustrates the short and long-term effect of salivation obtained through different types of non-DC sugar alcohols.

DETAILED DESCRIPTION OF THE INVENTION

The invention will now be described in more details with respect to certain aspects and embodiments of the invention. These aspects and embodiments are intended to be understood in connection with the rest of the description, including the Summary of the Invention and the Examples of the invention.

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in connection with the word comprising or containing denote "one or more." The expression "one or more" is intended to mean one, two, three or more.

As used herein, the term "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

As used herein the term "oral tablet" is considered a tablet for oral use. Particularly, the oral tablet is considered as formed by tableting, i.e. compression of a particle composition, comprising the mentioned population of particles. Thus, the tablet is considered a compressed tablet formed by a plurality of particles. Typically, the oral tablet may also be referred to as a tablet.

In the present context, the phrase "population of particles" refers to a statistical population of particles. The population of particles may be characterized by a number of different parameters, e.g. statistical parameters such as distribution of particles, average particle size, particle size distribution width, etc. The population of particles may have subpopulations, such as DC sugar alcohol particles, non-DC sugar alcohol particles, or in some embodiments, particles comprising gum base. The phrasing "population of particles" may in an embodiment of the invention be provided as a plurality of tableted particles and where the population of particles are tableted in one module or it may refer to a population of particles where some of the particles are tableted into one module and other particles are tableted into another module.

The term "particle size" relates to the ability of the particles to move through or be retained by sieve holes of a specific size. As used herein, the term "particle size" refers to the average particle size as determined according to European Pharmacopoeia 9.1 when using test method 2.9.38 particle size distribution estimation by analytical sieving, unless otherwise specifically is mentioned.

The term "particle" or similar wording is intended to denote a single, discrete composition of solid matter, such as a granule or individual elements in powder, having a certain size that may deviate considerable.

By the terms "water-insoluble gum base" or "gum base" or "gum base matrix" or similar wording is meant the mainly water-insoluble ingredients and hydrophobic gum base ingredients. The "gum base" may contain gum base polymers and plasticizers, waxes, emulsifiers, fats and/or fillers.

The term "natural resin", as used herein, means resinous compounds being either polyterpene derived from terpenes of natural origin or resinous compounds derived from gum rosin, wood rosin or tall-oil rosin.

The term "water-soluble chewing gum ingredients" intends to mean the mainly water-soluble and hydrophilic chewing gum ingredients.

In the present context, the term "non-DC areas" refers to small volumes or spaces formed during tableting from the non-DC particles of non-DC sugar alcohol. Moreover, each of the non-DC areas may be composed of a single non-DC sugar alcohol particle or may comprise several non-DC sugar alcohol particles. When the non-DC areas are distinct, i.e. not diffuse, the non-DC areas may be evenly distributed in the tablet, or at least one module thereof when the tablet comprises two or more modules. In such embodiments, where the non-DC areas are evenly distributed in in the tablet, or at least one module thereof, the non-DC areas may thus facilitate an even saliva generation in the mouth upon mastication.

The term "non-DC sugar alcohol particles" refers to particles of non-directly compressible (non-DC) sugar alcohol. It is noted that the terms "non-DC sugar alcohol particles" and "non-DC particles" are used interchangeably. In the present context, the non-DC sugar alcohol particles refer to particles which have not been preprocessed by granulation with e.g. other sugar alcohols or binders for the purpose of obtaining so-called direct compressible particles (DC). Thus, non-DC sugar alcohol particles are considered as particles consisting of non-DC sugar alcohol.

The term "DC sugar alcohol particles" refers to particles of direct compressible (DC) sugar alcohol. It is noted that the terms "DC sugar alcohol particles" and "DC particles" are used interchangeably. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC).

In the present context when the non-DC areas are referred to as "discrete", this signifies that the non-DC sugar alcohols are not continuously distributed, but present in the discrete areas corresponding to the discrete nature of the non-DC sugar alcohol particles.

The term "weight of the oral tablet" or similar wording meaning the same is defined in the present context as weight of the oral tablet, not including the weight of an outer coating, such as a hard coating, soft coating, and the like.

By the phrase "texture" is meant a qualitative measure of the properties of the oral tablet and of the overall mouth-feel experienced by the user during use. Thus, the term "texture" encompasses measurable quantities such as hardness as well as more subjective parameters related to the feel experienced by a user.

The term "in vivo use" intends to mean that the oral tablet is used by a human subject in an experimental setup of trained test persons according to statistically principles and that either the saliva of the human subject is subject to measurements or the oral tablet is subject to measurements.

The term "in vivo release" or "in vivo testing of release" or similar wording intends to mean that the oral tablet is tested as outlined in the examples.

The term "in vitro release" or "in vitro testing of release" or similar wording intends to mean that the oral tablet is tested according to the examples, in particular according to General Monograph 2.9.25 in European Pharmacopoeia, 5th ed.

The term "release" in the present context is intended to mean under "in vitro" conditions if not stated otherwise. In particular, the "release rate" during a certain period of time is intended to mean the amount in percentage of cannabinoids that is released during the period. In the present context the term "release" refers to the released substance being liberated from the water-soluble matrix. In some embodiments, the process of releasing a substance corresponds to the substance being dissolved in saliva.

The term "sustained release" or "extended release" is herein intended to mean prolonged release over time. The term "rapid release" or "quick release" or "high release" is herein intended to mean a higher content released for a given period of time. The term "controlled release" is intended to mean a release of a substance from an oral tablet by the aid of active use of the oral tablet in the oral cavity of the subject, whereby the active use is controlling the amount of substance released.

The term "delivery to the oral mucosa" or similar wording intends to mean that the oral tablet is tested according to the examples.

A "self-emulsifying agent" is an agent which will form an emulsion when presented with an alternate phase with a minimum energy requirement. In contrast, an emulsifying agent, as opposed to a self-emulsifying agent, is one requiring additional energy to form an emulsion.

When referring to induced saliva generation, it is noted that this induced saliva generation exceeds any saliva generation without the use of the tablet of the invention. Particularly, in an embodiment the induced saliva generation exceeds saliva generation when using conventional tablets without non-DC areas. Then, induced saliva generation is increased over any saliva generation associated with conventional products, e.g. by comparing with a tablet without non-DC sugar alcohol particles, or with a tablet where the discrete areas are based on DC sugar alcohol particles.

When referring to induced saliva generation, the saliva generation is tested using the following method.

Test subject abstain from eating and drinking at least 30 minutes before initiation of any test. Immediately before introducing of the tablet into the oral cavity, the test subject swallows. The test subject refrains from swallowing during the test.

Immediately after introducing of the tablet into the oral cavity, the test subject starts masticating the tablet at a frequency of 1 chew per second for 20 seconds. Then, saliva and any remains of the tablet is kept in the mouth within chewing for 10 second. 30 seconds after starting the test, the test subject discards saliva including any tablet fragments into a plastic cup, which is weighted. Saliva discarded also at 90 seconds after onset of mastication, at 180 seconds after onset of mastication, at 300 seconds after onset of mastication, at 420 seconds after onset of mastication, and at 600 seconds after onset of mastication. At all times, the test subject makes as little movement as possible, and refrains from swallowing.

In the following raw materials will refer to the mixed particles to be compressed into a tablet according to embodiments of the invention unless otherwise stated.

The following description outlines explanations of how the tablet of the invention may be produced and further details of what may be added to the inventive composition.

Typically, the process of manufacture of the inventive tablet may be performed in a single tablet press, such as a rotary tablet press. But it may be a benefit under some circumstances to apply a separate tablet press.

Preferably, the upper punch is convex which gives the upper face of the pressed tablet a concave form.

It should of course be noted that the shape of the punches may vary depending of the desired tablet shape.

In some embodiments of the invention, pressing of the tablets are performed at a force of 20 to 50 kN.

Important raw materials of the inventive tablet are non-DC sugar alcohol particles in combination with DC sugar alcohol particles.

The DC sugar alcohol particles refer to sugar alcohols known within the art as being direct compressible (DC).

The non-DC sugar alcohol particles refer to sugar alcohols known within the art as being non-directly compressible (DC).

According to a further embodiment of the invention, the applied non-DC sugar alcohol particles are best characterized as being non-directly compressible (non-DC). The use of non-DC sugar alcohols when compared to conventionally applied direct compressible sugar alcohol (DC) has shown remarkable effects to the user's perception of the delivery vehicle when chewed. This may partly be due to the somewhat larger size of non-DC sugar alcohol, when compared to DC sugar alcohol, but is may also be a result of a high content of sugar alcohol in the individual particles applied for compression. DC sugar alcohols, which for obvious reasons are marketed and applied for compression purposes, does not result in such improved salivation effect and mouthfeel.

It should be noted that the terminology non-DC is easily understood within the field of technology. Suppliers of sugar alcohol provides clear guidance to the user as for the ability for use in relation to compression of tablets. A non-DC particle in this connection is referred to as a particle which is not expressly recommended by the supplier for compression. Examples of a non-DC grade of erythritol includes Zerose™ erythritol 16952F supplied by Cargill. Further examples of non-DC sugar alcohol particles include non-DC xylitol as Xivia C from Dupont, non-DC isomalt as Isomalt GS from Beneo Paltinit, non-DC mannitol as Pearlitol from Roquette, non DC maltitol as Maltisorb. P200 from Roquette. Examples of a direct compressible (DC) grade of erythritol include Zerose™ DC 16966 also supplied by Cargill. Further examples of DC sugar alcohols include sorbitol particles provided as e.g. Neosor® P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab from Dupont.

Non-direct compressible (non-DC) sugar alcohols may include non-DC grades of Xylitol, non-DC grades of Erythritol, non-DC grades of Mannitol, non-DC grades of maltitol, non-DC grades of Lactitol, non-DC grades of Isomalt, or other suitable non-DC grades of sugar alcohols.

Direct compressible (DC) sugar alcohols may include sorbitol, which is DC by nature, DC grades of Xylitol, DC grades of Erythritol, DC grades of Mannitol, DC grades of maltitol, DC grades of Lactitol, DC grades of Isomalt or other suitable DC grades of sugar alcohols.

The present invention benefits from a synergy between the non-DC sugar alcohol particles and the DC sugar alcohol particles. The DC sugar alcohols may be e.g. sorbitol which is direct compressible by nature or it may be other sugar alcohols which has been preprocessed, e.g. by granulation with a suitable binder, to obtain particles which when compressed may encapsulate the non-DC sugar alcohol particles into a mechanically stable tablet. At the same time the non-DC sugar alcohol particles serves as a means for salivation which is both attractive to the user and also serves for the purpose of dissolving the DC sugar alcohol particles when the tablet is chewed as fast as possible.

The gum base is the masticatory substance of the oral tablet, which imparts the chew characteristics to the final product. The gum base typically defines the release profile and plays a significant role in the gum product. The gum base portion is retained in the mouth throughout the chew. The water-soluble portion disappears over a period of time during chewing.

According to embodiments of the invention, a preferred amount of gum base matrix in the final oral tablet is 30-75% by weight of the oral tablet before any optionally applied coating, such as 35-70% by weight of the oral tablet or 40-65% by weight of the oral tablet or 45-60% by weight of the oral tablet.

Elastomers provide the rubbery, elastomeric and bouncing nature to the gum, which varies depending on this ingredient's chemical structure and how it may be compounded with other ingredients. Elastomers suitable for use in the gum base and gum of the present invention may include natural or synthetic types. Polyvinyl acetate elastomer plasticizers are not considered elastomers according to the invention.

Elastomers may be selected from the group consisting of styrene-butadiene copolymers, polyisobutylene, isobutylene-isoprene copolymers, polyethylene, polyurethane or any combination thereof. Preferred elastomers are styrene-butadiene copolymers (SBR), polyisobutylene and isobutylene-isoprene copolymers (BR).

Styrene-butadiene type elastomers, or SBR as they may be called, typically are copolymers of from about 20:80 to 60:40 styrenes:butadiene monomers. The ratio of these monomers affects the elasticity of the SBR as evaluated by mooney viscosity. As the styrene:butadiene ratio decreases, the mooney viscosity decreases.

The structure of SBR typically consists of straight chain 1,3-butadiene copolymerized with phenylethylene (styrene). The average molecular weight of SBR is <600,000 g/mole.

Isobutylene-isoprene type elastomers, or butyl as they may be called, have molar percent levels of isoprene ranging from 0.2 to 4.0. Similar to SBR, as the isoprene:isobutylene ratio decreases, so does the elasticity, measured by mooney viscosity.

The structure of butyl rubber typically consists of branched 2-methyl-1,3-butadiene (isoprene) copolymerized with branched 2-methylpropene (isobutylene). The average molecular weight of BR is in the range from 150,000 g/mole to 1,000,000 g/mole.

Polyisobutylene, or PIB as they may be called, type elastomers are polymers of 2-methylpropene. The low molecular weight elastomers provide soft chew characteristics to the gum base and still provide the elastic qualities as do the other elastomers. Average molecular weights may range from about 30,000 to 120,000 g/mole and the penetration may range from about 4 millimeters to 20 millimeters. The higher the penetration, the softer the PIB. Similar to the SBR and butyl, the high molecular weight elastomers provide elasticity to the gum. Average molecular weight may range from 120,000 to 1,000,000 g/mole.

Polybutene range in average molecular weight from about 5.000 g/mole to about 30.000 g/mole.

Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang. Natural elastomers may also be applied in aspects of the present invention.

Elastomer plasticizers vary the firmness of the gum base. Their specificity on elastomer inter-molecular chain breaking (plasticizing) along with their varying softening points cause varying degrees of finished gum firmness and compatibility when used in base. Polyvinyl acetate elastomers plasticizers are examples of elastomer plasticizers of the present invention.

In some embodiments of the invention, the weight-average molecular weight (Mw) of the one or more polyvinyl acetate elastomer plasticizers is from 5,000 to 40,000. In some embodiments of the invention, the weight-average molecular weight (Mw) of the one or more polyvinyl acetate elastomer plasticizers is from 6,000 to 35,000. In some embodiments of the invention, the weight-average molecular weight (Mw) of the one or more polyvinyl acetate elastomer plasticizers is from 7,000 to 30,000. In some embodiments of the invention, the weight-average molecular weight (Mw) of the one or more polyvinyl acetate elastomer plasticizers is from 8,000 to 25,000. In some embodiments of the invention, the weight-average molecular weight (Mw) of the one or more polyvinyl acetate elastomer plasticizers is from 10,000 to 20,000.

In some embodiments of the invention, the viscosity of the one or more polyvinyl acetate elastomer plasticizers is from 1.0 to 3.0 mPa*s as measured according to ASTM D445-06 (10 wt. % in ethyl acetate), such as from 1.0 to 2.5 mPa*s.

In some embodiments of the invention, the K value of the one or more polyvinyl acetate elastomer plasticizers is from 15 to 33 as measured according to DIN 53726 (1 wt. % in acetone), such as from 18 to 30.

Generally, the term "polyvinyl acetate elastomer plasticizer" is intended to mean polyvinyl acetate having a weight-average molecular weight (Mw) of less than about 40,000.

Generally, the term "polyvinyl acetate elastomer" is intended to mean polyvinyl acetate having a weight-average molecular weight (Mw) of more than about 40,000.

In certain embodiments of the invention, the gum base comprises less than 10% by weight of polyvinyl acetate elastomer. In certain embodiments of the invention, the gum base comprises less than 5% by weight of polyvinyl acetate elastomer. In certain embodiments of the invention, the gum base comprises 2 to 6% by weight of polyvinyl acetate elastomer. In certain embodiments of the invention, the gum base comprises 3 to 5% by weight of polyvinyl acetate elastomer. In certain embodiments of the invention, the gum base is substantially free of polyvinyl acetate elastomer.

In certain embodiments of the invention, the gum base comprises 15-35% by weight of the one or more polyvinyl acetate elastomer plasticizers and less than 10% by weight of polyvinyl acetate elastomer. In certain embodiments of the invention, the gum base comprises 15-35% by weight of the one or more polyvinyl acetate elastomer plasticizers and less than 5% by weight of polyvinyl acetate elastomer. In certain embodiments of the invention, the gum base comprises 15-35% by weight of the one or more polyvinyl acetate elastomer plasticizers and 2 to 6% by weight of polyvinyl acetate elastomer.

Natural resins may be selected from ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the oral tablet comprises further ingredients selected from the group consisting of flavors, dry-binders, tableting aids, anti-caking agents, emulsifiers, antioxidants, enhancers, mucoadhesives, absorption enhancers, high intensity sweeteners, softeners, colors, active ingredients, water-soluble indigestible polysaccharides, water-insoluble polysaccharides or any combination thereof.

According to embodiments of the invention, the emulsifiers may be selected from the group consisting of sucrose ester of fatty acids (such as sucrose mono stearate), polyethylene glycol esters or ethers (PEG) (such as caprylocaproyl macrogol-8 glycerides and lauroyl macrogol-32-glycerides), mono- and diglyceride of fatty acids (such as glycerol monostearate, glycerol monolaurate, glyceryl behenate ester), acetic acid esters of mono- and diglycerides of fatty acids (Acetem), polyoxyethylene alkyl ethers, diacetyl tartaric ester of monoglycerides, lactylated monoglycerides, glycerophospholipids (such as lecithin), poloxamer (non-ionic block copolymer of ethylene oxide and propylene oxide), cyclodextrins, fatty acid esters of sorbitol (such as sorbitan monolaurate, sorbitan monostearate, sorbitan tristearate, polysorbates). Self-emulsifying emulsifiers may be phospholipids (Lecithin), Polysorbates (polysorbate 80).

SEDDS (self-emulsifying drug delivery system) may consist of hard or soft capsules filled with a liquid or a gel that consists of self-emulsifiers, one or more cannabinoids, oil (to dissolve the cannabinoids) and a surfactant. SEDDS may comprise of a blend or mixture of self-emulsifiers, one or more cannabinoids, oil (to dissolve the cannabinoids) and a surfactant. SEDDS may comprise granules comprising self-emulsifiers, one or more cannabinoids, oil (to dissolve the cannabinoids), one or more surfactants, solvent and co-solvents. Upon contact with gastric fluid, the SEDDS spontaneously emulsify due to the presence of surfactants. Many surfactants, however, are lipid based and interact with lipases in the GIT (gastro intestinal tract). This can lead to a reduced capability of the lipid-based surfactants to emulsify the one or more cannabinoids as well as the oil carrier, both reducing bioavailability.

In the present context, SEDDS is a solid or liquid dosage form comprising an oil phase, a surfactant and optionally a co-surfactant, characterized primarily in that said dosage form can form oil-in-water emulsion spontaneously in the oral cavity or at ambient temperature (referring generally to body temperature, namely 37° C.) with mild stirring. When a SEDDS enters the oral cavity, it is initially self-emulsified as emulsion droplets and rapidly dispersed throughout the oral cavity, and thus reducing the irritation caused by the direct contact of the drug with the mucous membrane of the oral cavity. In the oral cavity, the structure of the emulsion microparticulate will be changed or destroyed. The resulting microparticulate of micrometer or nanometer level can penetrate into the mucous membrane of the oral cavity, and the digested oil droplets enter the blood circulation, thereby significantly improving the bioavailability of the drug.

Particularly with respect to SEDDS, the formulation of the present invention may provide some clear benefits, both allowing a higher load of cannabinoids and at the same time offer improved sensorics properties of the formulation during use. Other advantages are also present.

In an embodiment of the invention, the one or more self-emulsifiers are selected from the group consisting of PEG-35 castor oil, PEG-6 oleoyl glycerides, PEG-6 linoleoyl glycerides, PEG-8 caprylic/capric glyceride, sorbitan monolaurate, sorbitan monooleate, polyoxyethylene (20) sorbitan monolaurate, polyoxyethylene (60) sorbitan monostearate, polyoxyethylene (80) sorbitan monooleate, lauroylpoloxyl-32 glycerides, stearoyl polyoxyl-32 glycerides, polyoxyl-32 stearate, propylene glycol mono laurate, propylene glycol di laurate, and mixtures and combinations thereof.

According to embodiments of the invention, flavors may be selected from the group consisting of coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Petroleum waxes aid in the curing of the finished oral tablet made from the oral tablet as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

Antioxidants prolong shelf life and storage of oral tablet, finished oral tablet or their respective components including fats and flavor oils.

Antioxidants suitable for use in oral tablet include butylated hydroxyanisole (BHA), butylated hydroxytoluene (BHT), betacarotenes, tocopherols, acidulants such as Vitamin C (ascorbic acid or corresponding salts (ascorbates)), propyl gallate, catechins, other synthetic and natural types or mixtures thereof.

Further oral tablet ingredients, which may be included in the oral tablet according to the present invention, include surfactants and/or solubilizers. As examples of types of surfactants to be used as solubilizers in an oral tablet according to the invention, reference is made to H. P. Fiedler, Lexikon der Hilfstoffe für Pharmacie, Kosmetik and Angrenzende Gebiete, pages 63-64 (1981) and the lists of approved food emulsifiers of the individual countries. Anionic, cationic, amphoteric or non-ionic solubilizers can be used. Suitable solubilizers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilizers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, block-copolymers of ethylene oxide and propyleneoxide and polyoxyethylene fatty alcohol ether. The solubilizer may either be a single compound or a combination of several compounds. In the presence of an active ingredient, such as the included one or more cannabinoids, the oral tablet may preferably also comprise a carrier known in the arts of oral tablet and active ingredients. Poloxamer F68 is a further highly suitable solubilizer.

High intensity artificial sweetening agents can also be used according to preferred embodiments of the invention. Preferred high intensity sweeteners include, but are not limited to sucralose, aspartame, salts of acesulfame, alitame, neotame, saccharin and its salts, cyclamic acid and its salts, glycyrrhizin, dihydrochalcones, thaumatin, monellin, monk fruit extract, advantame, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another oral tablet component such as a resinous compound.

Usage level of the high-intensity sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated high-intensity sweetener will be proportionately higher.

The oral tablet may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof. According to an embodiment of the invention, one preferred filler/texturizer is calcium carbonate.

A number of oral tablet components well known within the art may be applied within the scope of the present invention. Such components comprise but are not limited to waxes, fats, softeners, fillers, bulk sweeteners, flavors, antioxidants, emulsifiers, coloring agents, binding agents and acidulants.

In an embodiment of the invention, water-soluble ingredients comprise at least one sugar alcohol. The at least one sugar alcohol may be selected from the group consisting of xylitol, sorbitol, mannitol, maltitol, isomaltitol, isomalt, erythritol, lactitol, maltodextrin, hydrogenated starch hydrolysates, and combinations thereof.

In an aspect of the invention, the sugar alcohol of the invention may be replaced by one or more sugars, such as a sugar selected from the group consisting of dextrose, sucrose, maltose, fructose, lactose, and combinations thereof.

A method of manufacturing tabletted oral tablet with gum base according to the invention may be as follows:

Gum bases are typically prepared by adding an amount of the elastomer, elastomer plasticizer and filler to a heated (100° C.-120° C.) sigma blade mixer with a front to rear speed ratio of from about 1.2:1 to about 2:1, the higher ratio typically being used for gum base which requires more rigorous compounding of its elastomers.

The initial amounts of ingredients comprising the initial mass may be determined by the working capacity of the mixing kettle in order to attain a proper consistency and by the degree of compounding desired to break down the elastomer and increase chain branching. The higher the level of filler at the start or selection of a filler having a certain particle size distribution, the higher the degree of compounding and thus more of the elastomeric chain crosslinking are broken, causing more branching of the elastomer thus lower viscosity gum bases and thus softer final gum base and gum made from such a gum base. The longer the time of compounding, the use of lower molecular weight or softening point gum base ingredients, the lower the viscosity and firmness of the final gum base.

Compounding typically begins to be effective once the ingredients have massed together. Anywhere from 15 minutes to 90 minutes may be the length of compounding time.

Preferably, the time of compounding is from 20 minutes to about 60 minutes. The amount of added elastomer plasticizer depends on the level of elastomer and filler present. If too much elastomer plasticizer is added, the initial mass becomes over plasticized and not homogeneous.

After the initial ingredients have massed homogeneously and compounded for the time desired, the balance of the gum base ingredients are added in a sequential manner until a completely homogeneous molten mass is attained. Typically, any remainder of elastomer, elastomer plasticizer and filler, are added within 60 minutes after the initial compounding time. The filler and the elastomer plasticizer would typically be individually weighed and added in portions during this time. The optional waxes, softeners and antioxidants are typically added after the elastomer and elastomer plasticizers and during the next 60 minutes. Then the mass is allowed to become homogeneous before dumping.

Typical gum base processing times may vary from about one to about three hours, preferably from about 1½ to 2½ hours, depending on the formulation. The final mass temperature when dumped may be between 70° C. and 130° C. and preferably between 100° C. and 120° C. The completed molten mass is emptied from the mixing kettle into coated or lined pans, extruded or cast into any desirable shape and allowed to cool and solidify. Those skilled in the art will recognize that many variations of the above described procedure may be followed.

The gum base (or gum composition) may be further processed in an extruder where the gum composition is extruded through a die plate into a liquid filled chamber, resulting in particles directly applicable for tableting. Alternatively, the gum base may be milled into a desired particle range.

The water-soluble chewing gum ingredients of the tableted chewing gum may comprise softeners, sweeteners, high intensity sweeteners, flavoring agents, acidulants, fillers, antioxidants, and other components that provide desired attributes. Softeners typically constitute from about 0.5% to about 25.0% by weight of the chewing gum. The bulking agents generally comprise from about 5% to about 90%, preferably from about 20% to about 80% of the chewing gum. High-intensity sweeteners in gum typically may range from about 0.01 to 0.50 weight percent. Flavoring agents may be present in the chewing gum in an amount within the range of from about 0.1 to about 15.0 weight percent of the gum.

The water-soluble chewing gum ingredients of the tableted chewing gum composition according to the invention may be part of a first population of particles and subsequently subject to further processing in an extruder where the gum composition is extruded through a die plate into a liquid filled chamber, before tableting. However, the water-soluble chewing gum ingredients may also be part of a second population of particles or further populations of particles that are not exposed to a liquid filled chamber but applied together with the first population of particles to a tableting apparatus. In yet another embodiments, the water-soluble chewing gum ingredients may be part of the particles comprising water-insoluble gum base and not exposed to a liquid filled chamber but used directly in a tableting apparatus, optionally together with additional separate ingredients.

In an embodiment of the invention, the population of particles, comprising water-insoluble gum base, has an average diameter in the range from 0.1 to 2.5 mm.

In an embodiment of the invention, the population of particles, comprising water-insoluble gum base, has an average diameter in the range from 0.3 to 2.1 mm.

In an embodiment of the invention, the population of particles, comprising water-insoluble gum base, has an average diameter in the range from 0.8 to 1.4 mm.

The oral tablet according to the invention is manufactured by applying pressure to a content of particles by suitable compression means. The particles or powder is then pressed into a compact coherent tablet. The particles may for example comprise so-called primary particles or aggregated primary particles. When these are pressed, bonds are established between the particles or granules, thereby conferring a certain mechanical strength to the pressed tablet.

It should be noted that the above-introduced terms: powder, primary particles and aggregated primary particles may be somewhat misleading in the sense that the difference between primary particles and aggregated primary particles may very often be looked upon differently depending on the background of the user. Some may for instance regard a sweetener, such as sorbitol, as a primary particle in spite of the fact that sorbitol due to the typically preprocessing performed on sorbitol when delivered to the customer should rather be regarded as some sort of aggregated primary particles. The definition adopted in the description of this invention is that aggregated primary particles refer to macro-particles comprising more or less preprocessed primary particles.

When pressure is applied to the particles, the bulk volume is reduced, and the amount of air is decreased. During this process energy is consumed. As the particles come into closer proximity to each other during the volume reduction process, bonds may be established between the particles or granules. The formation of bonds is associated with a reduction in the energy of the system as energy is released. Volume reduction takes place by various mechanisms and different types of bonds may be established between the particles or granules depending on the pressure applied and the properties of the particles or granules. The first thing that happens when a powder is pressed is that the particles are rearranged under low compaction pressures to form a closer packing structure. Particles with a regular shape appear to undergo rearrangement more easily than those of irregular shape. As the pressure increases, further rearrangement is prevented, and subsequent volume reduction is obtained by plastic and elastic deformation and/or fragmentation of the tablet particles. Brittle particles are likely to undergo fragmentation, i.e. breakage of the original particles into smaller units. Plastic deformation is an irreversible process resulting in a permanent change of particle shape, whereas the particles resume their original shape after elastic deformation. Evidently, both plastic and elastic deformation may occur, when compressing an oral tablet.

Several studies of the bond types in pressed tablets have been made over the years, typically in the context of pharmaceuticals and several techniques of obtaining pressed tablets on the basis of available powders has been provided. Such studies have been quite focused on what happens when the volume reduction is performed and how the end-product may be optimized for the given purpose. Several refinements with respect to pressed tablets has for instance been made in the addition of for example binders in the tablet raw materials for the purpose of obtaining a sufficient strength to the final pressed tablet while maintaining acceptable properties, e.g. with respect to release.

Contrary to tableted chewing gum, conventional chewing gum (which is mentioned here for reference purposes) may be manufactured by sequentially adding the various chewing gum ingredients to a commercially available mixer known in the art where the finished gum base is already present. After the initial ingredients have been thoroughly mixed, the gum mass is discharged from the mixer and shaped into the desired form such as by rolling into sheets and cutting into sticks, extruded into chunks or casting into pellets. Generally, the ingredients of conventional chewing gum may be mixed by first melting the gum base and adding it to the running mixer. Colors, active agents and/or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor have been added. The entire mixing procedure typically takes from thirty to forty minutes, but longer mixing times may sometimes be required. Those skilled in the art will recognize that many variations of the above described procedure may be followed.

In accordance with the invention, the tableted oral tablet according to the invention may comprise about 0.1 to about 75% by weight of an outer coating applied onto the oral tablet centre. Thus, suitable coating types include hard coatings, film coatings and soft coatings of any composition including those currently used in coating of tableted oral tablet.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the consumer and it may moreover protect the oral tablet centres for various reasons. In a typical process of providing the oral tablet centres with a protective sugar coating, the oral tablet centres are successively treated in suitable coating equipment with aqueous solutions of crystallisable sugar such as sucrose or dextrose, which, depending on the stage of coating reached, may contain other functional ingredients, e.g. fillers, binding agents, colours, etc. In the present context, the sugar coating may contain further functional or active compounds including flavour compounds and/or active compounds.

In a typical hard coating process as it will be described in detail in the following, a suspension containing crystallisable sugar and/or polyol is applied onto the oral tablet centres and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished oral tablet element, such as about 10 to about 60% by weight, including about 15 to about 50% by weight.

In further useful embodiments, the outer coating of the oral tablet element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to an oral tablet centre of any of the above forms. The thickness of such a coating is usually between 20 and 100 µm.

Generally, the film coating is obtained by passing the oral tablet centres through a spray zone with atomized droplets of the coating materials in a suitable aqueous or organic solvent vehicle, after which the material adhering to the oral tablet centres is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers, also referred to as functional polymers are polymers that, in addition to its film-forming characteristics, confer a modified release performance with respect to active components of oral tablet. Such release modifying polymers include methylacrylate ester copolymers, ethylcellulose (EC) and enteric polymers designed to resist the acidic stomach environment. The latter group of polymers include; cellulose acetate phtalate (CAP), polyvinyl acetate phtalate (PVAP), shellac, metacrylic acid copolymers, cellulose acetate trimellitate (CAT) and HPMC. It will be appreciated that the outer film coating according to the present invention may comprise any combination of the above film-coating polymers.

According to the invention, the one or more cannabinoids may be selected from various cannabinoids.

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which may have high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that the additional components such as secondary and minor cannabinoids and the non-cannabinoid fraction have been substantially removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the cannabis plant and purified to the extent that other cannabinoids and non-cannabinoid components that are co-extracted with the cannabinoids have been substantially removed, such that the highly purified cannabinoid is greater than or equal to 95% (w/w) pure.

"Plant material" is defined as a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

In the context of this application the terms "cannabinoid extract" or "extract of cannabinoids", which are used interchangeably, encompass "Botanical Drug Substances" derived from cannabis plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of cannabis, "botanical drug substances" derived from cannabis plants do not include highly purified, Pharmacopoeial grade cannabinoids.

The term "*Cannabis* plant(s)" encompasses wild type *Cannabis sativa* and also variants thereof, including *cannabis* chemovars which naturally contain different amounts of the individual cannabinoids, *Cannabis sativa* subspecies *indica* including the variants var. indica and var. kafiristanica, *Cannabis indica*, *Cannabis ruderalis* and also plants which are the result of genetic crosses, self-crosses or hybrids thereof. The term "*Cannabis* plant material" is to be interpreted accordingly as encompassing plant material derived from one or more cannabis plants. For the avoidance of doubt it is hereby stated that "cannabis plant material" includes dried cannabis biomass.

Preferably the one or more cannabinoids are selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC. This list is not exhaustive and merely details the cannabinoids which are identified in the present application for reference.

So far, more than 120 different phytocannabinoids have been identified which are within the scope of the present invention.

Cannabinoids can be split into different groups as follows: Phytocannabinoids; Endocannabinoids; and Synthetic cannabinoids.

Cannabinoid receptors can be activated by three major groups of agonist ligands, for the purposes of the present invention and whether or not explicitly denominated as such herein, lipophilic in nature and classed respectively as: endocannabinoids (produced endogenously by mammalian cells); phytocannabinoids (such as cannabidiol, produced by the cannabis plant); and, synthetic cannabinoids (such as HU-210).

Phytocannabinoids can be found as either the neutral carboxylic acid form or the decarboxylated form depending on the method used to extract the cannabinoids. For example, it is known that heating the carboxylic acid form will cause most of the carboxylic acid form to decarboxylate.

Phytocannabinoids can also occur as either the pentyl (5 carbon atoms) or propyl (3 carbon atoms) variant. For example, the phytocannabinoid THC is known to be a CB1 receptor agonist whereas the propyl variant THCV has been discovered to be a CB1 receptor antagonist meaning that it has almost opposite effects.

According to the invention, examples of phytocannabinoids may be cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC.

The formulation according to the present invention may also comprise at least one cannabinoid selected from those disclosed in A. Douglas Kinghorn et al., Phytocannabinoids, Vol. 103, Chapter 1, pages 1-30.

Examples of endocannabinoids are molecules that activate the cannabinoid receptors within the body. Examples include 2-arachidonyl glycerol (2AG), 2-arachidonyl glyceryl ether (2AGE), arachidonyl dopamine, and arachidonyl ethanolamide (anandamide). Structurally related endogenous molecules have been identified that share similar structural features, but that display weak or no activity towards the cannabinoid receptors but are also termed endocannabinoids. Examples of these endocannabinoid lipids include 2-acyl glycerols, alkyl or alkenyl glyceryl ethers, acyl dopamines and N-acylethanolamides that contain alternative fatty acid or alcohol moieties, as well as other fatty acid amides containing different head groups. These include N-acylserines as well as many other N-acylated amino acids. Examples of cannabinoid receptor agonists are neuromodulatory and affect short-term memory, appetite, stress response, anxiety, immune function and analgesia.

In one embodiment the cannabinoid is palmitoylethanolamide (PEA) which is an endogenous fatty acid amide belonging to the class of nuclear factor agonists.

Synthetic cannabinoids encompass a variety of distinct chemical classes: the cannabinoids structurally related to THC, the cannabinoids not related to THC, such as (cannabimimetics) including the aminoalkylindoles, 1,5-diarylpyrazoles, quinolines, and arylsulfonamides, and eicosanoids related to the endocannabinoids. All or any of these cannabinoids can be used in the present invention.

It is preferred that the formulation comprises one or two primary cannabinoids, which are preferably selected from the group consisting of, cannabidiol (CBD) or cannabidivarin (CBDV), tetrahydrocannabinol (THC), tetrahydrocannabivarin (THCV), tetrahydrocannabinolic acid (THCA), cannabigerol (CBG) and cannabidiolic acid (CBDA) or a combination thereof. It is preferred that the formulation comprises cannabidiol and/or tetrahydrocannabinol.

Preferably, the oral tablet of the present invention may be used for the treatment or alleviation of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In a further aspect of the present invention, the oral cannabinoid formulation is suitable for use in the treatment of conditions requiring the administration of a neuroprotectant or anti-convulsive medication.

The oral cannabinoid formulation may be for use in the treatment of seizures.

The oral cannabinoid formulation may be for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, cannabis use disorder, post-traumatic stress disorder, anxiety, early psychosis, Alzheimer's disease, and autism.

The following non-limiting examples illustrate different variations of the present invention. The examples are meant for indicating the inventive concept; hence the mentioned examples should not be understood as exhaustive for the present. In particular, CBD is used as an exemplary compound, but may also be another cannabinoid.

FIGS. 1a and 1b illustrates an embodiment of an oral tablet 10 according to an embodiment of the invention. FIG. 1a shows the oral tablet from the side and FIG. 1b shows the tablet from above.

The composition and the way the tablet is or can be made is described elsewhere in the application and details regarding the structure and functioning of this tablet 10 is also indicated and explained further with reference to FIG. 4 and FIG. 5.

FIGS. 2a and 2b illustrates a two-module version of an oral tablet according to an embodiment of the invention. FIG. 2a shows the oral tablet from the side and FIG. 2b shows the tablet from above.

The composition and the way the tablet is made is described elsewhere in the application.

Details regarding the structure and functioning of this tablet 10 is also indicated and explained further with reference to FIGS. 4, 5 and 6.

The intention with this illustration is to give an example of a physical form, which may be applicable within the scope of the invention. The intention is also to illustrate how the term "a module" is understood and applied throughout the description, i.e. that a module is referring to a population of a plurality particles and the particles have been tableted together to form a module. The term module is applied to indicate that one module comprises one population of tableted particles and another module comprises another population of tabled particles. A population of particles in the present context is thus understood to refer to a plurality of particles. A singular particle is thus of course not understood as a module.

Modules are typically, but not necessarily, distinguishable by the human eye, in particular if the applied compounds in the different modules are formed by differently colored population of particles or mixtures of particles.

The oral tablet 20 comprises an upper module 21 and a lower module 22. The modules, here in the shapes of layers, are thus physically distinct and each comprises a population of particles which have been tableted. The population of the different modules, 21 and 22, may typically be different for many purposes. Examples include use for visual conception, for mechanical purposes e.g. providing strength, for medical purposes, and of course also for maximizing the desired effect of non-DC sugar alcohol contained in the tablet.

In a preferred embodiment, most of the applied non-DC sugar alcohol(s) is comprised in the upper module 21 and the lower module 22 is mostly comprised of DC-components, i.e. components such as sugar alcohols, fillers, flavors, colors etc. conventionally used for direct compression. In embodiments of the invention, a first module, here the lower module 22 may be regarded and applied as a support module supporting another module, here the upper module 21. The benefit of this division in the designing of properties is that the module containing the non-DC sugar alcohol particles may comprise substantial amounts of non-DC sugar alcohol particles even in spite of the fact that the modules own mechanical strength is substantially weakened, as the supporting modules structural strength may be designed to ensure that the overall structural strength of the tablet is sufficient to obtain the desired friability and tablet appearance. This multi-modular design approach is of even more interest as the tablets designed according to this principle benefits, in terms of disintegration and dissolving of the tablet matrix during mastication of the tablet, from the increased salivation effect obtained from the applied high content of non-DC sugar alcohol particles in the relatively weak module.

FIGS. 3a and 3b illustrates a three-module version of an oral tablet 30 according to an embodiment of the invention. FIG. 3a shows the oral tablet 30 from the side and FIG. 3b shows the tablet from above.

The illustrated tablet 30 comprises an upper module 31, and intermediate module 33 and a lower module 32.

The upper module 31 may, as explained in relation to the upper module of FIGS. 2a and 2b, be formed by a population of particles comprising an effective amount of non-DC sugar alcohol particles. The intermediate layer may comprise further non-DC sugar alcohol particles and one or more cannabinoids.

The lower module 32 may comprise substantial amounts of DC-particles such as sugar alcohol(s), fillers, some binder and other relevant ingredients enabling the lower module 32 to form a structural support for at least the upper module 31.

FIG. 4 illustrates a part 40 of a cross-section of one of the oral tablets in FIG. 1-3. The part of the oral tablet illustrated in FIG. 4 may thus correspond to a view of a part of the upper layers 21 or 31 or a part of the tablet 10.

Such part 40 of a tablet may within the scope of the invention comprise at least two different types of particles, namely non-DC sugar alcohol particles 41 and DC-particles 42. Preferred but non-limiting non-DC sugar alcohols are non-DC erythritol and non-DC xylitol as these non-DC sugar alcohols have shown effective to obtain the desired effect. The illustrated non-DC particles 41, although indicated on the figures with the same graphical expression may of course comprise non-DC sugar alcohol particles of the same type, but also comprise a mixture of two or more non-DC sugar alcohol particles.

The particles are evenly distributed amongst a plurality of DC particles 42 within the specified module. The DC particles 42, although indicated in the figure as same type particles may include different types of DC sugar alcohol particles, flavor particles, binders, etc. The intention with the figure is to illustrate that the non-DC sugar alcohol particles 41 in practice have to be homogenously distributed amongst the DC particles 42 in the final oral tablet 40. It may not be enough that the non-DC particles and DC particles are mixed homogenously at some stage during the preparation of the tableting process. The homogenous mix should preferably be maintained in the final oral tablet 40 in order to promote the desired effect and to obtain a mechanically stable tablet. A further advantageous effect of the evenly distributed non-DC sugar alcohol particles may be obtained through an advantageous and increased salivation during mastication of a tablet.

The understanding and conception of the evenly distribution of the non-DC sugar alcohol particles in the relevant tablet module may in practical terms be very difficult to define as such definitions are very difficult to monitor and control during the processing of the tablet but it has been possible to establish an industrial scale process, where the mixture containing the substantial amounts of non-DC sugar alcohol(s) may be established all the way through the process into the final tablet. Such process may e.g. be validated by test manufacturing of a sequence of tablets where the variation of the non-DC sugar alcohol content of the manufactured tablets are determined.

It is noted that the non-DC particles 41 forms small sub-areas or sub spaces in the final oral tablet or the relevant module of the final tablet, e.g. the upper modules 21 and 31. These sub-areas are elsewhere in the present application referred to as discrete non-DC areas and may be formed by single non-DC particles or very small groups of these non-DC particles. These discrete non-DC areas are thus intended to be contained within a matrix formed by DC-sugar alcohol particles or other DC-particles.

The non-DC areas, in the present embodiment, the non-DC sugar alcohol particles 41 are thus included in substantial amounts in the tablet and from a mechanical perspective supported and contained by the DC-particles 42 and together forming a matrix which, when chewed, may bring the non-DC sugar alcohol particles 42 into contact with the oral cavity and promote salivation. The promoted salivation, together with relatively weak mechanical structure of the module or tablet comprising the non-DC sugar alcohol particles induces a fast breakup of the tablet and thereby pushes the non-DC particles into contact with the oral cavity in a way which is completely different from compressed tablets made from DC-sugar alcohol particles, such as granulated erythritol or xylitol.

The non-DC areas may thus result in induced saliva generation upon mastication of the tablet and also induce and promote a very fast and pleasant dissolving of the tablet matrix when compared to conventional compressed tablets.

The one or more cannabinoids may be present as both DC and non-DC particles as long as the cannabinoids as such does not interfere significant with other compounds.

If the cannabinoids are located in with non-DC particles, the amount should be kept low enough to ensure the mechanical stability of the tablet or modules or alternatively compensated by relevant DC-particles or binders. It should be noted that such a compensation should be carefully considered as this compensation may both compromise salivation effect and texture/mouthfeel during mastication.

FIG. 5 illustrates a part of a cross-section of one of the oral tablets in FIG. 1-3. The part of the oral tablet illustrated in FIG. 5 may thus correspond a view of a part of the upper modules 21 or 31 or the tablet 10.

In terms of components applied, the tablet part illustrated in FIG. 5 may largely correspond to the above-described embodiment of FIG. 4, but now the tablet part comprises larger sized non-DC particles 51 containing in a compression of particles of DC particles 52.

The intention with the present FIG. 5 is merely to indicate that in particular the non-DC sugar alcohol particles may be larger in size than the DC particles and it is also noted in this context that the use of larger sized non-DC sugar alcohol particles may indeed increase the obtained salivation or the desired effect.

FIG. 6 illustrates a particular transition in a tablet 60 with two adjacent modules according to an embodiment of the invention. The presently illustrated part of such tablet may e.g. refer to the transition between the modules 21 and 22 of the tablet 20 as seen in FIG. 2*a*. The tablet 60 comprises non-DC sugar alcohol particles 61 and DC particles 62 in one module and another module comprising DC particles 63. The understanding of a module is here easily conceivable as the population of non-DC sugar alcohol particles 61 and DC particles 62 forms one module and the population of DC particles 63 forms another module. Often, the compositions of the DC sugar alcohol particles 62 and the DC sugar alcohol particles 63 may be different, depending on the specific circumstances.

Again, in relation to FIG. 5 and FIG. 6, cannabinoids may be present as both DC and non-DC particles as long as the cannabinoids as such does not interfere significant with other compounds. If the cannabinoids are located with the non-DC particles, the amount should be kept low enough to ensure the mechanical stability of the tablet or modules or alternatively compensated by relevant DC-particles or binders. It should be noted that such a compensation should be carefully considered as this may both compromise salivation effect and texture/mouthfeel during mastication.

Particles comprising gum base, may also be present both as non-DC and DC particles, although DC-particles comprising gum base are highly preferred over non-DC gum base-containing particles. When applying particles comprising gum base, these particles are preferably but not necessarily included in a supporting module as DC particles 63 e.g. with mixed with sugar alcohol particles 63 as illustrated in FIG. 6.

The above illustrated modules are all designed as layers. It is stressed that other shapes of modules may be applicable within the scope of the invention. Non-limiting examples are modules having a sphere shape, diamond shape, oval shape, cone shape, etc. All the relevant shapes must of course be adapted to fit the tableting process according to known measures within the art.

EXAMPLES

Example 1

Component with CBD Extract 50%

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on top of one or more sugar alcohol particles. After mixing until CBD was homogeneously distributed in the one or more sugar alcohol particles, the mixture was sieved through a 1400 microns sieve.

Example 2

Component with CBD Extract 10%

CBD extract with a 10% content of CBD provided by Medical Hemp (batch number MH131B Gold), was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on top of one or more sugar alcohol particles. After mixing until CBD was homogeneously distributed in the one or more sugar alcohol particles, the mixture was sieved through a 1400 microns sieve.

Example 3

Component with CBD Isolate with a Solvent

CBD isolate from cannabis plant tissues (phytocannabinoid) with a 98.5% content of CBD provided by Medical Hemp (batch number MH18212) was dissolved in a 96% ethanol solution. The ratio between the CBD isolate and ethanol was 1:1. Once CBD was dissolved in ethanol, the CBD isolate was applied in a premix with one or more sugar alcohol particles. After mixing until CBD was homogeneously distributed in the one or more sugar alcohol particles, the mixture was sieved through a 1400 microns sieve.

Example 4

Component with CBD Isolate without a Solvent

CBD isolate from cannabis plant tissues (phytocannabinoid) with a 98.5% content of CBD provided by Medical Hemp (batch number MH18212) was added as free powder and mixed with one or more sugar alcohol particles. After mixing until CBD was homogeneously distributed in the one or more sugar alcohol particles, the mixture was sieved through a 1400 microns sieve.

Example 5

Component including Microcrystalline Cellulose

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on microcrystalline cellulose (MCC). Mixing was conducted until the CBD was homogeneously distributed in the MCC. Optionally, the CBD-MCC premix could be further mixed with one or more sugar alcohol particles. The mixture was sieved through a 1400 microns sieve.

Example 6

Component including Silicium Dioxide Carrier

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on silicium dioxide (SiO2). Mixing was conducted until the CBD was homogeneously distributed in the SiO2. Optionally, the CBD-SiO2 premix could be further mixed with one or more sugar alcohol particles. The mixture was sieved through a 1400 microns sieve.

Example 7

Component including Hyperporous Silica Magnesium-Alumino-Metasilicates

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on hyperporous silica magnesium-alumino-metasilicates. Mixing was conducted until the CBD was homogeneously distributed in the hyperporous silica magnesium-alumino-metasilicates. Optionally, the CBD-hyperporous silica magnesium-alumino-metasilicates premix could be further mixed with one or more sugar alcohol particles. The mixture was sieved through a 1400 microns sieve.

Example 8

Preparation of Cannabinoid Component with Emulsifier and Oil

Solution of Labrafil M 1944 CS and Maisine CC (1:1) was mixed. CBD isolate from Example 3 or CBD extract from Example 1 was added and dissolved in the solution to obtain a 33% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 9

Preparation of Cannabinoid Component with Emulsifier, Oil and Co-Solvent

Solution of 60% Labrafac Lipophile WL1349 and 25% Labrasol and 15% Propylene Glycol was mixed. CBD isolate from Example 3 or CBD extract from Example 1 was added and dissolved in the solution to obtain a 33% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 10

Preparation of Cannabinoid Component with Solid Solubilizer

Gelucire 50/13 was melted at app. 60° C. and CBD isolate from Example 3 or CBD extract from Example 1 was added and dissolved in the melted solution to obtain a 50% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 11

Preparation of Cannabinoid Component with Emulsifier and Co-Solvent

CBD extract from Example 1 was preheated at 60° C., until it was in liquid form and then dissolved in Propylene Glycol. Labrasol ALF was then added to obtain a 17% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 12

Preparation of Cannabinoid Component with Solubilizer

CBD extract from Example 1 was preheated at 60° C. until it was in liquid form. After the preheating process, the extract was applied in a premix with Soluplus and mixed until the premix was homogeneous, obtaining a 12.5% premix of CBD. The premix was then mixed with one or more sugar alcohols. After mixing until CBD was homogeneously distributed in the one or more sugar alcohols, the mixture was sieved through a 1400 microns sieve.

Example 13

Preparation of Cannabinoid Component with Cyclodextrin and Emulsifier

CBD isolate from Example 3 was added and dissolved in polysorbate 80 to obtain a 10% solution of CBD. The 10% CBD solution was slowly added and mixed into a solution with 4% cyclodextrin to form a CBD-cyclodextrin complex. The water was removed, whereupon the complex was applied in a premix with one or more sugar alcohols. After mixing until the CBD-cyclodextrin complex was homogeneously distributed in the one or more sugar alcohols, the mixture was sieved through a 1400 microns sieve.

Example 14

A: Preparation of Tablet with One Layer

A cannabinoid component from either one of Examples 1 to 13 and tablet component were blended in a mixing container at about 7-9 rpm and optionally loaded with processing aid in order to improve free-flowing properties of the particles and to avoid stickiness. In a first step, half the tablet component was added to a mixing container. High-intensity sweetener (HIS), flavors and the cannabinoid component were added to the container, after which the other half of the tablet component was added. The mixture was tumbled at 7-9 rpm for 10 minutes. A processing aid was added and the mixture was tumbled at 7-9 rpm for another 2 minute. Hereafter, the mixture was ready for tableting.

The mixture was subsequently led to a standard tablet pressing machine (3090i, available from Fette GmbH) comprising dosing apparatus (P 3200 C, available from Fette GmbH, Germany) and pressed into tablets. The filling depth in the apparatus was 11 mm and the diameter 15.0 mm. The tablets were pressed using a pressing pressure of 20 kN, unless stated otherwise, and optionally prepressed with a pressing pressure of 1-7 kN. There were 75 punches on the rotor, and the rotor speed used was 11 rpm.

B: Preparation of Tablet with Two Layers

A layer with the same ingredients, and prepared in the same way, as in Example 14A was tableted on top of the first layer from Example 14A. The ratios of the ingredients were different in this second layer.

Examples 15

Composition of Cannabinoid Tablets with Two Layers

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 60 to 40. The tablets contained an amount of 5 mg CBD. The tablets had a weight of 1.5 g.

TABLE 1

| Tablet number | 100 | |
|---|---|---|
| Raw material name | Content [%] Layer 1-0.9 g | Content [%] Layer 2-0.6 g |
| Pre-mixture component | | |
| Isomalt DC | 20.00 | |
| CBD-extract (loaded 50%) | 1.111 | |
| Tablet component | | |
| Isomalt DC | 24.22 | |
| Erythritol non-DC | 50.0 | |
| Xylitol DC | | 94.75 |
| Flavor | 4.1 | 4.7 |
| HIS | 0.07 | 0.05 |
| Processing aids | 0.5 | 0.5 |
| Total | 100 | 100 |

It was secured that CBD was thoroughly mixed into the premixture.
The CBD could be added to layer 1 as showed here in table 1, or in layer 2 or in both layers.

Examples 16

Composition of Cannabinoid Tablets with Two Layers and Gum Base

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 55 to 45. The tablets contained an amount of 10 mg CBD. The tablets had a weight of 1.6 g.

TABLE 2

| Tablet number | 101 | |
|---|---|---|
| Raw material name | Content [%] Layer 1-0.88 g | Content [%] Layer 2-0.72 g |
| Pre-mixture component | | |
| Isomalt DC | 20.00 | |
| CBD-extract (loaded 50%) | 2.273 | |
| Tablet component | | |
| Gum base | | 80 |
| Isomalt DC | 23.16 | 14.93 |
| Erythritol non-DC | 50.0 | |
| Flavor | 4.0 | 4.0 |
| HIS | 0.07 | 0.07 |
| Processing aids | 0.5 | 1.0 |
| Total | 100 | 100 |

It was secured that CBD was thoroughly mixed into the premixture.
Gum base was provided as gum base granules.
The CBD could be added to layer 1 as showed here in table 2, or in layer 2 or in both layers.

Examples 17

Composition of Cannabinoid Tablets with Two Layers and No Non-DC Sugar Alcohol

Cannabinoid tablets based on the procedure in Example 14B were made with the formulations outlined in the examples below. In all of the tablet examples, the amount of the various ingredients is given as % by weight of the tablet. The weight ratio of layer 1 to layer 2 was 55 to 45. The tablets contained an amount of 10 mg CBD. The tablets had a weight of 1.6 g.

TABLE 3

| Tablet number | 102 | |
|---|---|---|
| Raw material name | Content [%] Layer 1-0.88 g | Content [%] Layer 2-0.72 g |
| Pre-mixture component | | |
| Isomalt DC | 20.00 | |
| CBD-extract (loaded 50%) | 2.273 | |
| Tablet component | | |
| Gum base | | 80 |
| Isomalt DC | 74.657 | 15.43 |
| Erythritol non-DC | | |
| Flavor | 2.5 | 3.5 |
| HIS | 0.07 | 0.07 |
| Processing aids | 0.5 | 1.0 |
| Total | 100 | 100 |

It was secured that CBD was thoroughly mixed into the premixture.
Gum base was provided as gum base granules.

Examples 18

Composition of Cannabinoid Tablets with One Layer and Gum Base

Cannabinoid tablets based on the procedure in Example 14A were made with the formulations outlined in the examples below. In all of the tablet examples, the amount of the various ingredients was given as % by weight of the tablet. The tablets contained an amount of 10 mg CBD. The tablets had a weight of 1.35 g.

TABLE 4

| | Tablet number | |
|---|---|---|
| Raw material name | 103 Zapliq Content [%] | 104 Std. Content [%] |
| Pre-mixture component | | |
| Isomalt DC | 20.00 | 20.00 |
| CBD-extract (loaded 50%) | 1.481 | 1.481 |
| Tablet component | | |
| Gum base | 36 | 36 |
| Isomalt DC | 7.75 | 37.75 |
| Erythritol non-DC | 30.0 | |
| Flavor | 4.2 | 4.2 |
| HIS | 0.07 | 0.07 |
| Processing aids | 0.5 | 0.5 |
| Total | 100 | 100 |

It was secured that CBD was thoroughly mixed into the premixture.
Gum base was provided as gum base granules.
Std. was prepared as a comparative example without non-DC erythritol.
Zapliq was prepared as an inventive example.

Example 19

Composition of Cannabinoid Tablets with Different CBD Source

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 55 to 45. The tablets contained an amount of 10 mg CBD. The tablets had a weight of 1.6 g.

TABLE 5

| | Tablet Number | | | | |
|---|---|---|---|---|---|
| Raw material name | 105 Content [%] Layer 1-0.88 g | 106 Content [%] Layer 1-0.88 g | 107 Content [%] Layer 1-0.88 g | 108 Content [%] Layer 1-0.88 g | 105-108 Content [%] Layer 2-0.72 g** |
| Pre-mixture component | | | | | |
| Isomalt DC | 20 | 20 | 20 | 20 | |
| CBD-extract (loaded 50%) | 2.273 | | | 2.273 | |

TABLE 5-continued

| | Tablet Number | | | | |
|---|---|---|---|---|---|
| Raw material name | 105 Content [%] Layer 1-0.88 g | 106 Content [%] Layer 1-0.88 g | 107 Content [%] Layer 1-0.88 g | 108 Content [%] Layer 1-0.88 g | 105-108 Content [%] Layer 2-0.72 g** |
| CBD isolate (loaded 98.5%)-dissolved in ethanol 1:1 (Example 3) | | 1.154 | 1.154* | | |
| Tablet component | | | | | |
| Gum base | | | | | 80 |
| Isomalt DC | 22.96 | 24.08 | 24.08 | 21.46 | 14.93 |
| Erythritol non-DC | 50 | 50 | 50 | 50 | |
| Flavor | 4.2 | 4.2 | 4.2 | 4.2 | 4.0 |
| HIS | 0.07 | 0.07 | 0.07 | 0.07 | 0.07 |
| Processing aids | 0.5 | 0.5 | 0.5 | 0.5 | 1.0 |
| Xanthan gum | | | | 1.5 | |
| Total | 100 | 100 | 100 | 100 | 100 |

It was secured that CBD was thoroughly mixed into the premixture.
*CBD isolate has been added loosely to the pre-mixture-not dissolved in ethanol-according to the procedure in Example 4 (deviation of the procedure in Example 3).
**Layer 2 is the same for all tablets 105-108.

Example 20

Composition of Cannabinoid Tablets with Different Pre-Mixture

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 55 to 45. The tablets contained an amount of 10 mg CBD. The tablets had a weight of 1.6 g.

Example 21

Composition of Cannabinoid Tablets with Different Self-Emulsifying Drug Delivery System (SEDDS) Components Cannabinoid tablets based on the procedure in Example 14A were made with the formulations outlined in the examples below. In all of the tablet examples, the amount of the various ingredients was given as % by weight of the tablet. The tablets contained an amount of 10 mg CBD. The tablets had a weight of 1 g.

TABLE 6

| | Tablet Number | | | | |
|---|---|---|---|---|---|
| Raw material name | 109 Content [%] Layer 1-0.88 g | 110 Content [%] Layer 1-0.88 g | 111 Content [%] Layer 1-0.88 g | 112 Content [%] Layer 1-0.88 g | 109-112 Content [%] Layer 2-0.72 g* |
| Pre-mixture component | | | | | |
| Maltitol DC | 20 | 20 | 20 | 20 | |
| MCC | 4.5 | 4.5 | | | |
| SiO2 | | | 4.5 | — | |
| Hyperporous carrier** | | | — | 4.5 | |
| CBD-extract (loaded 50%) | 2.273 | | 2.273 | 2.273 | |
| CBD isolate (loaded 98.5%)-dissolved in ethanol 1:1 (Example 3) | | 1.154 | | | |
| Tablet component | | | | | |
| Gum base | | | | | 80 |
| Maltitol DC | 18.46 | 19.58 | 18.46 | 18.46 | 14.93 |
| Erythritol non-DC | 50 | 50 | 50 | 50 | |
| Flavor | 4.2 | 4.2 | 4.2 | 4.2 | 4.0 |
| HIS | 0.07 | 0.07 | 0.07 | 0.07 | 0.07 |
| Processing aids | 0.5 | 0.5 | 0.5 | 0.5 | 1.0 |
| Total | 100 | 100 | 100 | 100 | 100 |

It was secured that CBD was thoroughly mixed into the premixture.
*Layer 2 is the same for all tablets 109-112.
Hyperporous carrier** hyperporous silica magnesium-alumino-metasilicates.

TABLE 7

It was secured that CBD was thoroughly mixed into the premixture.

| Raw material name | Lozenge Number | | | | | |
|---|---|---|---|---|---|---|
| | 113 Content [%] | 114 Content [%] | 115 Content [%] | 116 Content [%] | 117 Content [%] | 118 Content [%] |
| Pre-mixture component | | | | | | |
| Maltitol DC | 27.0 | 27.0 | 27.0 | 30.0 | 30.0 | 30.0 |
| CBD-extract (loaded 50%) | | | | 2.0 | 2.0 | |
| CBD isolate (loaded 98.5%) | 1.0 | 1.0 | 1.0 | | | |
| Labrafil M 1944 CS | 1.0 | | | | | |
| Gelucire 50/13 | | | 1.0 | | | |
| Labrasol ALF | | 0.5 | | 2.0 | | |
| Maisine CC | 2.0 | | | | | |
| Labrafac Lipophile WL 1349 | | 1.2 | | | | |
| Propylene Glycol | | 0.3 | | 2.0 | | |
| Soluplus | | | | | 6.0 | |
| CBD-cyclodextrin | | | | | | 6.0 |
| Tablet component | | | | | | |
| Gum base | 25 | 25 | 25 | 25 | 25 | 25 |
| Maltitol DC | 14.23 | 15.23 | 16.23 | 9.23 | 7.23 | 9.23 |
| Erythritol non-DC | 25 | 25 | 25 | 25 | 25 | 25 |
| Flavors | 4.2 | 4.2 | 4.2 | 4.2 | 4.2 | 4.2 |
| HIS | 0.07 | 0.07 | 0.07 | 0.07 | 0.07 | 0.07 |
| Processing aids | 0.5 | 0.5 | 0.5 | 0.5 | 0.5 | 0.5 |
| Total | 100 | 100 | 100 | 100 | 100 | 100 |

Examples 22

Further Compositions of Cannabinoid Tablets with Two Layers (Layer 1)

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 60 to 40. The tablets contained an amount of 5 mg CBD. The tablets had a weight of 1.5 g.

TABLE 8

Tablet compositions for first layer of bi-layered tablets containing variants of non-DC sugar alcohols.
Amounts are given in wt-9 of the respective layer of tablet.

| Raw material (wt %)-First layer | 119 | 120 | 121 | 122 | 123 | 124 |
|---|---|---|---|---|---|---|
| Pre-mixture component | | | | | | |
| Isomalt DC | 20.00 | 20.00 | 20.00 | 20.00 | 20.00 | 20.00 |
| CBD-extract (loaded 50%) | 1.11 | 1.11 | 1.11 | 1.11 | 1.11 | 1.11 |
| Tablet component | | | | | | |
| Non-DC Xylitol | 50 | | | | | |
| Soibitol** | | 50 | | | | |
| Non-DC Isomalt | | | 50 | | | |
| Non-DC Erythritol | | | | 50 | | |
| Non-DC Mannitol | | | | | 50 | |
| Non-DC Maltitol | | | | | | 50 |
| DC Isomalt Soibitol | 22.64 | 22.64 | 22.64 | 22.64 | 22.64 | 22.64 |
| Flavor | 4 | 4 | 4 | 4 | 4 | 4 |
| HIS | 0.25 | 0.25 | 0.25 | 0.25 | 0.25 | 0.25 |
| Magnesium Stearate | 1 | 1 | 1 | 1 | 1 | 1 |
| Binder HPC | 1 | 1 | 1 | 1 | 1 | 1 |
| Total | 100 | 100 | 100 | 100 | 100 | 100 |
| Resistance to crunchiness [N]* | 160 | >350 | 190 | 142 | 90 | 174 |
| Friability | 0.74 | 0.25 | 0.63 | 1.30 | 1.45 | 1.00 |

*Method limitation means maximum resistance to crunch can be measured up to 350N.
**non-granulated sorbitol. It was secured that CBD was thoroughly mixed into the premixture.

Examples 23

Further Compositions of Cannabinoid Tablets with Two Layers (Layer 1)

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 60 to 40. The tablets contained an amount of 5 mg CBD. The tablets had a weight of 1.5 g.

TABLE 9

Tablet compostions for first layer of bi-layered tablets containing variants of non-DC sugar alcohols.
Amounts are given in wt-9 of the respective layer of tablet.

| Raw material (wt %)-First layer | 125 | 126 | 127 | 128 | 129 | 130 |
|---|---|---|---|---|---|---|
| Pre-mixture component | | | | | | |
| Isomalt DC | 20.00 | 20.00 | 20.00 | 20.00 | 20.00 | 20.00 |
| CBD-extract (loaded 50%) | 1.11 | 1.11 | 1.11 | 1.11 | 1.11 | 1.11 |
| Tablet component | | | | | | |
| Non-DC Xylitol | 50 | | | | | |
| Soibitol** | | 50 | | | | |
| Non-DC Isomalt | | | 50 | | | |
| Non-DC Erythritol | | | | 50 | | |
| Non-DC Mannitol | | | | | 50 | |
| Non-DC Maltitol | | | | | | 50 |
| DC Isomalt Soibitol | 23.14 | 23.14 | 23.14 | 23.14 | 23.14 | 23.14 |
| Flavor | 4 | 4 | 4 | 4 | 4 | 4 |

TABLE 9-continued

Tablet compostions for first layer of bi-layered tablets containing variants of non-DC sugar alcohols. Amounts are given in wt-9 of the respective layer of tablet.

| Raw material (wt %)-First layer | 125 | 126 | 127 | 128 | 129 | 130 |
|---|---|---|---|---|---|---|
| HIS | 0.25 | 0.25 | 0.25 | 0.25 | 0.25 | 0.25 |
| Magnesium Stearate | 1 | 1 | 1 | 1 | 1 | 1 |
| Binder HPC | 0.5 | 0.5 | 0.5 | 0.5 | 0.5 | 0.5 |
| Total | 100 | 100 | 100 | 100 | 100 | 100 |
| Resistance to crunchiness [N]* | 190 | >350 | 270 | 170 | 120 | 210 |
| Friability | 0.65 | 0.12 | 0.87 | 1.13 | 1.25 | 0.88 |

*Method limitation means maximum resistance to crunch can be measured up to 350N.
**non-granulated sorbitol. It was secured that CBD was thoroughly mixed into the premixture.

Examples 24

Further Compositions of Cannabinoid Tablets with Two Layers (Layer 2)

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 60 to 40. The tablets contained an amount of 5 mg CBD. The tablets had a weight of 1.5 g.

TABLE 10

| Raw material (wt %)-Second layer | 119-130 | 119-130 | 119-130 |
|---|---|---|---|
| DC Maltitol | 94.75 | | |
| DC Xylitol | | 94.75 | — |

TABLE 10-continued

| Raw material (wt %)-Second layer | 119-130 | 119-130 | 119-130 |
|---|---|---|---|
| DC Isomalt | | | 94.75 |
| Flavor | 4 | 4 | 4 |
| HIS | 0.25 | 0.25 | 0.25 |
| Processing aid | 1 | 1 | 1 |
| Total | 100 | 100 | 100 |

Tablet compositions for second layer of bi-layered tablets containing variants of DC sugar alcohols. Amounts are given in wt-% of the respective layer of tablet.

A specification of relevant compounds applied in all of the examples explained above is listed below.

HPC: Hydroxy propyl cellulose. Klucel Nutra D from Ashland
Non-DC Xylitol: Xivia C from Dupont
Non-granulated Sorbitol from PharmSorbidex from Cargill
Non-DC Isomalt: Isomalt GS from Beneo Paltinit
Non-DC Mannitol: Pearlitol from Roquette
Non-DC Maltitol: Maltisorb. P200 from Roquette
Non-DC Erythritol: Zerose 16952 from Cargill
DC Erythrito—Zerose 16966 from Cargill
DC Xylitol—Xylitab 200 from Dupont
DC Isomalt—Isomalt DC 101 from Beneo Paltinit
DC Mannitol—Pearlitol SD200 from Roquette
DC Maltitol—Sweetpearl 300 DC from Roquette Example 25

Composition of Cannabinoid Tablets with Different CBD Source

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 55 to 45. The tablets contained an amount of 10 mg CBD. The tablets had a weight of 1.6 g.

TABLE 11

| | Tablet Number | | | | |
|---|---|---|---|---|---|
| Raw material name | 131 Content [%] Layer 1-0.88 g | 132 Content [%] Layer 1-0.88 g | 133 Content [%] Layer 1-0.88 g | 134 Content [%] Layer 1-0.88 g | 131-134 Content [%] Layer 2-0.72 g** |
| Pre-mixture component | | | | | |
| Isomalt DC | 20 | 20 | 20 | 20 | |
| CBD-extract (loaded 50%) | 2.273 | | | 2.273 | |
| CBD isolate (loaded 98.5%)-dissolved in ethanol 1:1 (Example 3) | | 1.154 | 1.154* | | |
| Tablet component | | | | | |
| Isomalt DC | 22.96 | 24.08 | 24.08 | 21.46 | 94.93 |
| Erythritol non-DC | 50 | 50 | 50 | 50 | |
| Flavor | 4.2 | 4.2 | 4.2 | 4.2 | 4.0 |
| HIS | 0.07 | 0.07 | 0.07 | 0.07 | 0.07 |
| Processing aids | 0.5 | 0.5 | 0.5 | 0.5 | 1.0 |
| Xanthan gum | | | | 1.5 | |
| Total | 100 | 100 | 100 | 100 | 100 |

It was secured that CBD was thoroughly mixed into the premixture.
*CBD isolate has been added loosely to the pre-mixture-not dissolved in ethanol-according to the procedure in Example 4 (deviation of the procedure in Example 3).
**Layer 2 is the same for all tablets 131-134.

Example 26

Composition of Cannabinoid Tablets with Different Pre-Mixture

Cannabinoid tablets based on the procedure in Example 14B were made with the formulations outlined in the examples below. In all of the tablet examples, the amount of the various ingredients was given as % by weight of the tablet. The weight ratio of layer 1 to layer 2 was 55 to 45. The tablets contained an amount of 10 mg CBD. The tablets had a weight of 1.6 g.

TABLE 12

| | Tablet Number | | | | |
|---|---|---|---|---|---|
| Raw material name | 135 Content [%] Layer 1-0.88 g | 136 Content [%] Layer 1-0.88 g | 137 Content [%] Layer 1-0.88 g | 138 Content [%] Layer 1-0.88 g | 135-138 Content [%] Layer 2-0.72 g* |
| Pre-mixture component | | | | | |
| Maltitol DC | 20 | 20 | 20 | 20 | |
| MCC | 4.5 | 4.5 | | | |
| SiO2 | | | 4.5 | | |
| Hyperporous carrier** | | | | 4.5 | |
| CBD-extract (loaded 50%) | 2.273 | — | 2.273 | 2.273 | |
| CBD isolate (loaded 98.5%)-dissolved in ethanol 1:1 | | 1.154 | | | |
| Tablet component | | | | | |
| Maltitol DC | 18.46 | 19.58 | 18.46 | 18.46 | 94.93 |
| Erythritol non-DC | 50 | 50 | 50 | 50 | |
| Flavor | 4.2 | 4.2 | 4.2 | 4.2 | 4.0 |
| HIS | 0.07 | 0.07 | 0.07 | 0.07 | 0.07 |
| Processing aids | 0.5 | 0.5 | 0.5 | 0.5 | 1.0 |
| Total | 100 | 100 | 100 | 100 | 100 |

It was secured that CBD was thoroughly mixed into the premixture.
*Layer 2 is the same for all tablets 135-138.
Hyperporous carrier** hyperporous silica magnesium-alumino-metasilicates.

Example 27

Composition of Cannabinoid Tablets with Different Self-Emulsifying Drug Delivery System (SEDDS) Components Cannabinoid tablets based on the procedure in Example 14A were made with the formulations outlined in the examples below. In all of the tablet examples, the amount of the various ingredients was given as % by weight of the tablet. The tablets contained an amount of 10 mg CBD. The tablets had a weight of 1 g.

TABLE 13

It was secured that CBD was thoroughly mixed into the premixture.

| | Lozenge Number | | | | | |
|---|---|---|---|---|---|---|
| Raw material name | 139 Content [%] | 140 Content [%] | 141 Content [%] | 142 Content [%] | 143 Content [%] | 144 Content [%] |
| Pre-mixture component | | | | | | |
| Maltitol DC | 27.0 | 27.0 | 27.0 | 30.0 | 30.0 | 30.0 |
| CBD-extract (loaded 50%) | | | | | 2.0 | 2.0 |

TABLE 13-continued

It was secured that CBD was thoroughly mixed into the premixture.

| | Lozenge Number | | | | | |
|---|---|---|---|---|---|---|
| Raw material name | 139 Content [%] | 140 Content [%] | 141 Content [%] | 142 Content [%] | 143 Content [%] | 144 Content [%] |
| CBD isolate (loaded 98.5%) (Example 4) | 1.0 | 1.0 | 1.0 | | | |
| Labrafil M 1944 CS | 1.0 | | | | | |
| Gelucire 50/13 | | | 1.0 | | | |
| Labrasol ALF | | 0.5 | | 2.0 | | |
| Maisine CC | 2.0 | | | | | |
| Labrafac Lipophile WL 1349 | | 1.2 | | | | |
| Propylene Glycol | | 0.3 | | 2.0 | | |
| Soluplus | | | | | 6.0 | |
| CBD-cyclodextrin | | | | | | 6.0 |
| Tablet component | | | | | | |
| Maltitol DC | 39.23 | 40.23 | 41.23 | 34.23 | 32.23 | 34.23 |
| Erythritol non-DC | 25 | 25 | 25 | 25 | 25 | 25 |

TABLE 13-continued

It was secured that CBD was thoroughly mixed into the premixture.

| | Lozenge Number | | | | | |
|---|---|---|---|---|---|---|
| Raw material name | 139 Content [%] | 140 Content [%] | 141 Content [%] | 142 Content [%] | 143 Content [%] | 144 Content [%] |
| Flavors | 4.2 | 4.2 | 4.2 | 4.2 | 4.2 | 4.2 |
| HIS | 0.07 | 0.07 | 0.07 | 0.07 | 0.07 | 0.07 |
| Processing aids | 0.5 | 0.5 | 0.5 | 0.5 | 0.5 | 0.5 |
| Total | 100 | 100 | 100 | 100 | 100 | 100 |

Example 28

In Vivo Testing of Release for Tablets with Gum Base

A sample was chewed with a chewing frequency of 60 chews pr. minute for 3 or 5 minutes in a test panel of 8 test persons. Test subject abstain from eating and drinking at least 30 minutes before initiation of any test. The test person was a healthy person appointed on an objective basis according to specified requirements. After 3 or 5 minutes, the content of CBD was measured in the remaining residue. The tablet was subject to triple measurements for each of the 8 test persons, giving a total of 24 measurements for each sample. An average of the 24 measurements was calculated and the weight % release was calculated based on the original content of CBD in the sample. The content of CBD was measured in the remaining residue. The residue was positioned in a flask and weighted. Subsequently, an organic solvent was added for dissolution purposes, and the mixture was mixed on a laboratory shaker overnight.

The organic phase was diluted and centrifuged. The supernatant was injected directly into an HPLC system and analyzed by an assay method.

Example 29

In Vitro Testing of Release for Tablets with Gum Base

In vitro release of CBD was established by means of a chewing machine (Dissolution Test for Chewing Gums, General Monograph 2.9.25. In European Pharmacopoeia, 5th ed). A chewing chamber was filled with 20 ml buffer (phosphate buffer pH 7.4). The tablet sample was placed in the chamber and the chewing machine was initiated at 20 degrees Celsius with 1 chew per second. After 3 or 5 minutes of chewing, the machine was stopped and the sample (residue) was placed in a vial. If more release time points were needed (release profile), the chewing buffer must be exchanged with 20 ml of fresh buffer every five minutes. The content of CBD was measured in the remaining residue. The residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method.

Example 30

In Vivo Testing of Release for Tablets

When referring to induced saliva generation, the saliva generation is tested using the following method. Test subject abstain from eating and drinking at least 30 minutes before initiation of any test. Immediately before introducing of the tablet into the oral cavity, the test subject swallows. The test subject refrains from swallowing during the test. Immediately after introducing of the tablet into the oral cavity, the test subject starts masticating the tablet at a frequency of 1 chew per second for 20 seconds. Then, saliva and any remains of the tablet is kept in the mouth within chewing for 10 second. 30 seconds after starting the test, the test subject discards saliva including any tablet fragments into a plastic cup, which is weighted. Saliva discarded also at 90 seconds after onset of mastication, at 180 seconds after onset of mastication, at 300 seconds after onset of mastication, at 420 seconds after onset of mastication, and at 600 seconds after onset of mastication. At all times, the test subject makes as little movement as possible, and refrains from swallowing. The saliva was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method.

Example 31

CBD Delivered to the Oral Mucosa for Tablets with Gum Base

A sample was chewed in vivo with a chewing frequency of 60 chews pr. minute for 5 minutes in a test panel of 8 test persons. Test subject abstain from eating and drinking at least 30 minutes before initiation of any test. The test person was not allowed to swallow during the procedure. After one minute, saliva was obtained from the test person and collected in a vessel for later analysis. In tests for 5 minutes release, the same procedure was followed until 5 minutes where the last saliva sample was collected and added to the same vessel for aggregated analysis. The test person was a healthy person appointed on an objective basis according to specified requirements. The aggregated saliva sample was collected after 5 minutes, and the content of CBD was measured in the saliva. The content of CBD was also measured in the remaining residue. The residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method. The residue and saliva were subject to triple measurements for each of the 8 test persons, giving a total of 24 measurement for each sample. An average of the 24 measurements was calculated and the weight % release was calculated. By comparing the amount of CBD in the remaining residue and the amount of CBD in the saliva, the amount of CBD delivered to the oral mucosa could be estimated.

Example 32

CBD Delivered to the Oral Mucosa for Tablets without Gum Base

A test panel of 8 test persons has been used for this test. Test subject abstain from eating and drinking at least 30 minutes before initiation of any test. Immediately before introducing of the tablet into the oral cavity, the test subject swallows. The test subject refrains from swallowing during the test. Immediately after introducing of the tablet into the oral cavity, the test subject starts masticating the tablet at a frequency of 1 chew per second for 20 seconds. Then, saliva and any remains of the tablet is kept in the mouth within chewing for further 10 seconds. The saliva is subsequently moved around in the mouth and after 1 minute after starting the test, the test subject discards saliva including any tablet fragments into a plastic cup, which is weighted. The test is repeated with a new tablet under the same conditions as for the 1 minute test but instead of discarding saliva after 1 minute, the saliva is moved around and kept for 3 minutes in the mouth without swallowing before the test subject discards saliva including any tablet fragments into a plastic cup, which is weighted. The saliva samples collected was analyzed for content of CBD The saliva was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method by a HPLC method. The saliva were subject to 3 triple measurements for each of the 8 test persons, giving a total of 24 measurement for each sample. An average of the 24 measurements was calculated. By comparing the amount of CBD released (100%), and the amount of CBD in the saliva, the amount of CBD delivered to the oral mucosa could be estimated.

Example 33

Sensoric Evaluation Test Set-Up

Apart from dissolution measurements, either in vivo or in vitro for a tablet with or without a content of gum base, sensoric tests were performed on all examples to reveal very important characteristics and properties of the tablets. These sensoric parameters are important as indicators of the structure of the tablet composition. The structure is the underlying guidance as to how the tablet resembles the structure of a comparative tablet, which is set as the standard in the test series, i.e. the tablets are compared to each other in the test series of preferably 5 samples. The test set-up was composed of 8 test persons in a test panel. Each of the test persons were healthy individuals appointed on an objective basis according to specified requirements. The sensory analysis was performed according to ISO 4121-2003 in testing conditions following ISO 8589. The result is an average of the results of the 8 individuals.

The test persons gave a rating from "+" to "+++++", where "+" is poor and "+++++" is excellent and comparable to the standard, i.e. "+++++" means that the tablet was comparable to the standard and "+" means that the tablet was very far from comparable to the standard. "0" indicated that it was not tested.

Six different parameters were tested in a test panel:

| Mouth-feel | Friability | Flavor | Sweet-ness | Off-notes | Watering effect | Disintegration |
| --- | --- | --- | --- | --- | --- | --- |

"Mouthfeel"—the general impression of the tablet when placed in the mouth with respect to elements such as crumbling, juiciness, roughness and texture.

"Friability"—the impression of the tablet when placed in the mouth and chewing is commenced. For instance, a very hard and viscous structure gave a very low rating and a very brittle structure also gave a very low rating. Friability is measured according to European Pharmacopoeia 9.1, test method 2.9.7. by using a pharmaceutical friability-tester PTF 10E from Pharma Test.

"Flavor"—the overall impression of the tablet during chewing with respect to flavor. For instance, a very low flavor experience gave a very low rating and a too high flavor experience that was not comparable to the standard also gave a very low rating.

"Sweetness"—the overall impression of the taste of the tablet during chewing with respect to sweetness. For instance, if the sweetness was decreasing rapidly, a very low rating was given and if the sweetness was too high giving an uncomfortable feeling, a very low rating was also given.

"Off-notes"—the overall impression of the off-note from the one or more cannabinoids in the composition during chewing. For instance, if off-notes (grass, bitter notes, irritation in the throat) were experienced in the throat, a low rating was given and if other uncomfortable sensations was experienced, a low rating was also given.

"Watering effect"—the overall impression of the watering effect from the combination of the one or more cannabinoids and non-DC sugar alcohol particles in the formulation.

"Disintegration"—the overall impression of the disintegration of the tablet upon chewing. For instance, a low rate was given with very a poor disintegration.

Example 34

Evaluation

TABLE 14

| Ex | Total sensory experience (Good/Acceptable (Acc)/Poor) | Suitable fast dissolving chewable tablet | Initial watering effect 1-5 (1 low; 5 high) |
| --- | --- | --- | --- |
| 119 | Acc | A bit hard initial chew, disintegrate with crunchy feeling, many big particles for a long time | 4 |
| 120 | Poor | Unacceptable hard chew-not chewable or complete dissolvable within the first 30 seconds. | 2 |
| 121 | Poor | Very hard and difficult to disintegrate. Saliva increases but with many big non-dissolved particles within the first 30 sec. | 3 |
| 122 | Good | Nice crunchy fast dissolving tablet | 5 |
| 123 | Poor | Soft initial chew, different mouth feel. Sticky feeling. Does not dissolve fast enough or provide pleasant watering effect | 2 |
| 124 | Poor | Hard initial chew. Very crumble and sandy feeling. Salivation generation but sandy liquid feeling | 4 |

Evaluation of samples 119-124 in accordance with Example 24-for all three variant in the second layer.

It was first of all noted that the watering effect was considered relatively high for samples 119, 121, 122 and 124, i.e. the examples based on non-DC Xylitol, non-DC Isomalt, non-DC Erythritol and non-DC Maltitol. The watering effect is considered to be representative or equal to the elsewhere described salivation effect.

The test panel clearly indicated that the overall chewing process and the mouthfeel was no less than impressive in relation to sample 122 based on non-DC Erythritol. It was also noted that the test panel identified non-DC Xylitol of sample 119 and non-DC Maltitol of sample 124 as having an impressive watering effect when compared to e.g. the sorbitol-based samples.

As a supplement to the sensory evaluation, the resistance to crunching and friability was measured and indicated in the samples 119-130, i.e. with reference to a bi-layer tablet with a first layer as indicated in Table 8 and Table 9 and a second layer based primarily on DC xylitol as indicated in Table 10.

The resistance to crunching is determined according to European Pharmacopoeia 9.1, test method 2.9.8. by using a pharmaceutical resistance to crunching tester model Pharma Test type PTB 311.

Friability is measured according to European Pharmacopoeia 9.1, test method 2.9.7. by using a pharmaceutical friability-tester PTF 10E from Pharma Test.

FIG. 7 illustrates a measuring of the salivation effect related to the above-mentioned samples 119-130, where different non-DC sugar alcohols have been applied. Sorbitol is applied as a reference as a representative DC sugar alcohol.

ISX1 refers to the non-DC xylitol sample 119,
ISX2 refers to the sorbitol sample 120,
ISX3 refers to the non-DC isomalt sample 121,
ISX4 refers to the non-DC sample 122,
ISX5 refers to the non-DC mannitol sample 123 and
ISX6 refers to the non-DC maltitol sample 124.

The saliva generation as measured with reference to FIG. 7 and the associated examples is defined in the description as a definition with reference to the measuring method.

The results of the measured saliva generation are illustrated in FIG. 7, where saliva generation is measured in grams as a function of time (minutes).

It is noted that the saliva generation from all non-DC sugar alcohols are impressive in the beginning, but it is also noted that saliva generation over time is no less than astonishing in relation to ISX4, i.e. the non-DC erythritol sample 122. It is thus noted that the salivation effect is increased a very long time after the major part of non-DC erythritol based tablet has been swallowed or collected during the measurement. It is also observed that the relatively low initial perceived salivation effect of sample 120, i.e. the sorbitol-based example is confirming the sensory evaluation as mentioned above.

The invention claimed is:

1. An oral chewable tablet for delivery of cannabinoids to mucosal surfaces comprising a population of particles and one or more cannabinoids, the population of particles comprising a) directly compressible (DC) sugar alcohol particles and b) non-directly compressible (non-DC) sugar alcohol particles being particles consisting essentially of pure sugar alcohol, the non-DC particles providing the tablet with a plurality of discrete non-DC areas, wherein the tablet comprises said non-DC sugar alcohol particles in an amount of at least 10% by weight of the tablet.

2. The oral chewable tablet according to claim 1, wherein at least 30% by weight of the non-DC sugar alcohol particles have a particle size above 500 μm.

3. The oral chewable tablet according to claim 1, wherein the one or more cannabinoids are present in an amount of 0.1 to 400 mg.

4. The oral chewable tablet according to claim 1, wherein the one or more cannabinoids are selected from the group consisting of cannabidiol (CBD), cannabidiolic acid (CBDA), cannabidivarin (CBDV), salts and derivatives thereof.

5. The oral tablet according to claim 1, wherein the one or more cannabinoids are selected from the group consisting of tetrahydrocannabinol (THC), tetrahydrocannabinolic acid (THCA), tetrahydrocannabivarin (THCV), salts and derivatives thereof.

6. The oral chewable tablet according to claim 1, wherein the non-DC sugar alcohol particles are selected from the group consisting of non-DC particles of erythritol, maltitol, xylitol, isomalt, lactitol, mannitol, and combinations thereof.

7. The oral chewable tablet according to claim 1, wherein said DC sugar alcohol particles are selected from the group consisting of DC particles of sorbitol, erythritol, xylitol, lactitol, maltitol, mannitol, isomalt, and combinations thereof.

8. The oral chewable tablet according to claim 1, wherein the tablet has a weight ratio between said non-DC sugar alcohol particles and said DC sugar alcohol particles, which is between 0.3 and 0.7.

9. The oral chewable tablet according to claim 1, wherein saliva generation upon mastication of the tablet is induced compared to a tablet without non-DC sugar alcohol particles.

10. The oral chewable tablet according to claim 1, wherein the tablet generates more than 1.5 mL saliva within 30 seconds from onset of mastication.

11. The oral chewable tablet according to claim 1, wherein the tablet further comprises a self-emulsifying system that when hydrated with saliva upon oral administration forms an emulsion for delivery of the one or more cannabinoids to a mucosal surface.

12. The oral chewable tablet according to claim 11, wherein the self-emulsifying system comprises one or more emulsifiers and one or more oil carriers.

13. The oral chewable tablet according to claim 11, wherein the self-emulsifying system comprises one or more emulsifiers, one or more oil carriers and one or more solubilizers.

14. The oral chewable tablet according to claim 1, wherein the one or more cannabinoids are present in a premixture.

15. The oral chewable tablet according to claim 14, wherein the premixture is present in an amount of 5 to 50% by weight of the tablet.

16. The oral chewable tablet according to claim 14, wherein the one or more cannabinoids are present in a premixture and reversibly adsorbed onto one or more solid particles, wherein a weight ratio of the one or more cannabinoids relative to the one or more solid particles is from 1:30 to 1:1.

17. The oral chewable tablet according to claim 1, wherein said population of particles is comprised in a first module of the tablet and a second population of particles is comprised in a second module of the tablet.

18. The oral chewable tablet according to claim 17, wherein the second module comprises DC sugar alcohol particles in an amount of at least 50% by weight of the second module.

19. The oral chewable tablet according to claim 1, wherein the one or more cannabinoids comprise at least one phytocannabinoid that forms part of an extract.

20. The oral chewable tablet according to claim 1, wherein the one or more cannabinoids comprise at least one isolated cannabinoid.

21. The oral tablet according to claim 1, wherein the one or more cannabinoids comprise at least one endocannabinoid or endocannabinoid-like compound.

22. The oral tablet according to claim 1, wherein the one or more cannabinoids comprise at least one water-soluble cannabinoid.

23. An oral chewable tablet for delivery of cannabinoids to mucosal surfaces comprising a population of particles and one or more cannabinoids, the population of particles comprising a) directly compressible (DC) sugar alcohol particles and b) non-directly compressible (non-DC) sugar alcohol particles being particles consisting essentially of pure sugar alcohol, the non-DC particles providing the tablet with a plurality of discrete non-DC areas, wherein the tablet has a weight ratio between said non-DC sugar alcohol particles and said DC sugar alcohol particles, which is between 0.3 and 0.7.

24. The oral chewable tablet according to claim 23, wherein the non-DC sugar alcohol particles are selected from the group consisting of non-DC particles of erythritol, maltitol, xylitol, isomalt, lactitol, mannitol, and combinations thereof.

25. An oral chewable tablet for delivery of cannabinoids to mucosal surfaces comprising a population of particles and one or more cannabinoids, the population of particles comprising a) directly compressible (DC) sugar alcohol particles and b) non-directly compressible (non-DC) sugar alcohol particles being particles consisting essentially of pure sugar alcohol, the non-DC particles providing the tablet with a plurality of discrete non-DC areas, wherein the one or more cannabinoids are present in a premixture and reversibly adsorbed onto one or more solid particles, wherein a weight ratio of the one or more cannabinoids relative to the one or more solid particles is from 1:30 to 1:1.

26. The oral chewable tablet according to claim 25, wherein the premixture is present in an amount of 5 to 50% by weight of the tablet.

27. An oral chewable tablet for delivery of cannabinoids to mucosal surfaces comprising a population of particles and one or more cannabinoids, the population of particles comprising a) directly compressible (DC) sugar alcohol particles and b) non-directly compressible (non-DC) sugar alcohol particles being particles consisting essentially of pure sugar alcohol, the non-DC particles providing the tablet with a plurality of discrete non-DC areas, wherein said population of particles is comprised in a first module of the tablet and a second population of particles is comprised in a second module of the tablet, wherein the second module comprises DC sugar alcohol particles in an amount of at least 50% by weight of the second module.

* * * * *